(12) United States Patent
Hashimoto et al.

(10) Patent No.: US 9,375,363 B2
(45) Date of Patent: Jun. 28, 2016

(54) DISPOSABLE WEARING ARTICLE

(71) Applicant: UNICHARM CORPORATION, Shikokuchuo-shi, Ehime (JP)

(72) Inventors: Tatsuya Hashimoto, Kanonji (JP); Toshifumi Otsubo, Kanonji (JP); Tetsuo Okubo, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/385,438

(22) PCT Filed: Mar. 27, 2013

(86) PCT No.: PCT/JP2013/058915
§ 371 (c)(1),
(2) Date: Sep. 15, 2014

(87) PCT Pub. No.: WO2013/146839
PCT Pub. Date: Oct. 3, 2013

(65) Prior Publication Data
US 2015/0032072 A1 Jan. 29, 2015

(30) Foreign Application Priority Data

Mar. 29, 2012 (JP) ................................ 2012-077889
Mar. 8, 2013 (JP) ................................ 2013-047366

(51) Int. Cl.
*A61F 13/15* (2006.01)
*A61F 13/494* (2006.01)
(Continued)

(52) U.S. Cl.
CPC ....... *A61F 13/4942* (2013.01); *A61F 13/15593* (2013.01); *A61F 13/15699* (2013.01);
(Continued)

(58) Field of Classification Search
CPC .................... A61F 31/49406; A61F 31/49413; A61F 31/4942; A61F 31/4946; A61F 31/49466; A61F 31/4948; A61F 31/49493; A61F 31/49017; A61F 31/49039; A61F 31/49061; A61F 31/455; A61F 31/4556
See application file for complete search history.

(56) References Cited

U.S. PATENT DOCUMENTS 6,706,029 B1 * 3/2004 Suzuki et al. ............ 604/385.28
8,308,706 B2 * 11/2012 Fukae ......................... 604/393
(Continued)

FOREIGN PATENT DOCUMENTS

CN    1220866 A    6/1999
EP    2520259 A1    11/2012
(Continued)

OTHER PUBLICATIONS

International Search Report mailed Jun. 4, 2013 in International Patent Application No. PCT/JP2013/058915, filed Mar. 27, 2013 with English language translation.
(Continued)

*Primary Examiner* — Bradley Philips
(74) *Attorney, Agent, or Firm* — Hauptman Ham, LLP

(57) ABSTRACT

A disposable wearing article includes an annular elastic waist panel having a front waist panel and a rear waist panel joined to each other and a crotch panel provided with an absorbent structure and connected to the elastic waist panels. Respective inner end edges of the front and rear waist panels cooperate with lateral edges of the crotch panel extending in a longitudinal direction to form a pair of leg-openings' peripheries. The crotch panel includes a pair of leg sheets connected to both lateral edges of the absorbent structure. The respective leg sheets include inner regions adjoining to the absorbent structure and outer regions adjoining the inner regions so that the inner regions rise above the absorbent structure along both lateral edges of the absorbent structure to define the leg-openings' peripheries and the outer regions are bent outwardly in the transverse direction so as to define the leg-openings' peripheries.

19 Claims, 18 Drawing Sheets

(51) Int. Cl.
*A61F 13/496* (2006.01)
*A61F 13/49* (2006.01)

(52) U.S. Cl.
CPC ......... *A61F13/15756* (2013.01); *A61F 13/496* (2013.01); *A61F 13/49012* (2013.01); *A61F 13/49015* (2013.01); *A61F 13/49017* (2013.01); *A61F 13/49061* (2013.01); *A61F 13/49406* (2013.01); *A61F 2013/4948* (2013.01)

(56) References Cited

U.S. PATENT DOCUMENTS

| | | | |
|---|---|---|---|
| 2002/0045875 A1* | 4/2002 | Minato et al. | 604/385.28 |
| 2002/0065502 A1* | 5/2002 | Shimizu et al. | 604/385.28 |
| 2004/0243083 A1* | 12/2004 | Matsuda et al. | 604/385.01 |
| 2006/0122571 A1* | 6/2006 | Chang et al. | 604/385.27 |
| 2007/0149943 A1* | 6/2007 | Miyamoto | 604/385.28 |
| 2010/0106123 A1 | 4/2010 | Fukae | |

FOREIGN PATENT DOCUMENTS

| | | |
|---|---|---|
| JP | 11-188058 A | 7/1999 |
| JP | 11-188061 A | 7/1999 |
| JP | 2008-508082 A | 3/2008 |
| JP | 2009-018095 A | 1/2009 |
| JP | 2011-098052 A | 5/2011 |
| WO | 2011/081027 A1 | 7/2011 |

OTHER PUBLICATIONS

Written Opinion of the International Searching Authority mailed Jun. 4, 2013 in corresponding International Application No. PCT/JP2013/058915 filed Mar. 27, 2013.

Extended European Search Report dated Oct. 13, 2015, corresponding to European Patent Application No. 13768188.8.

* cited by examiner

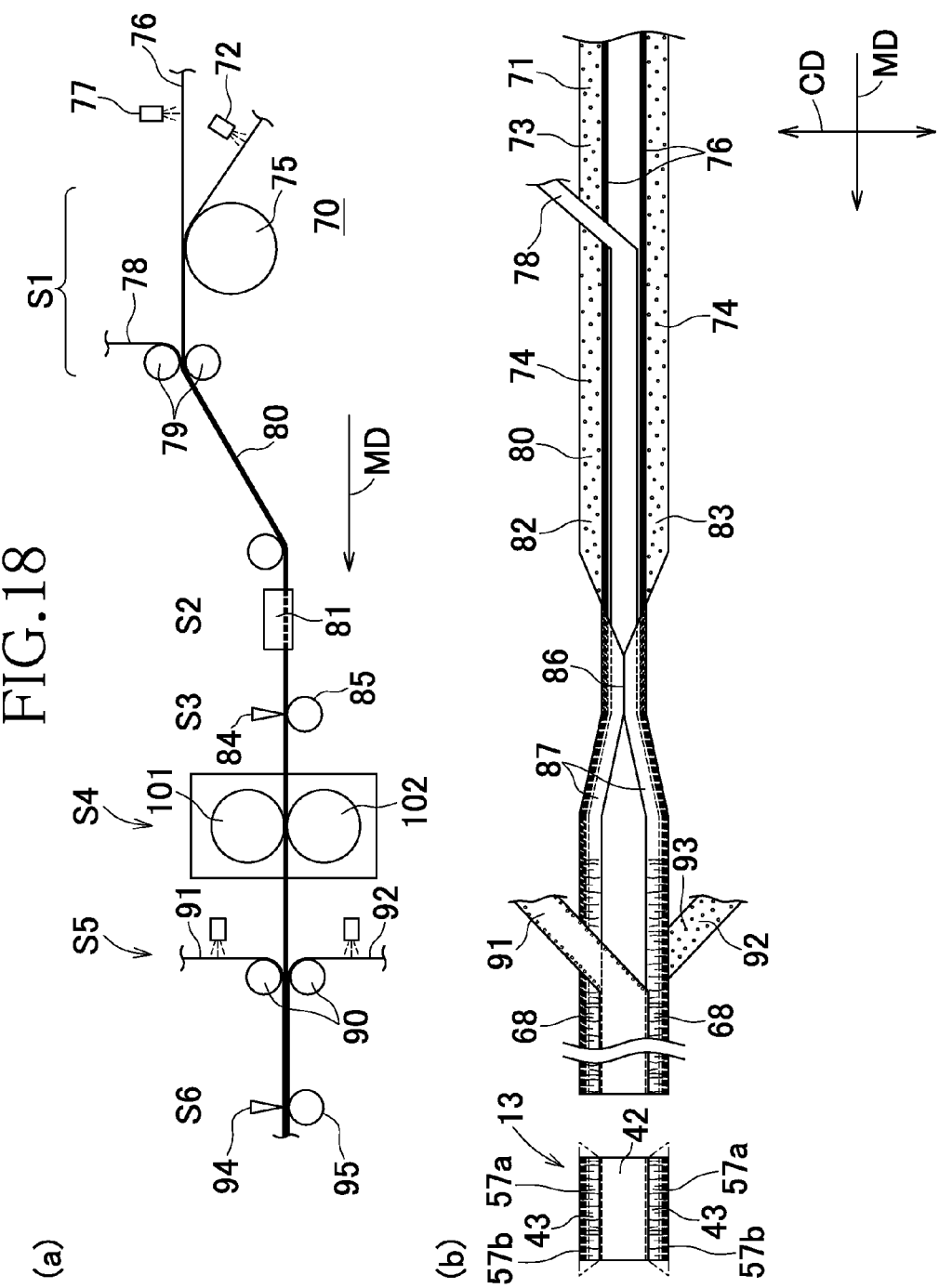

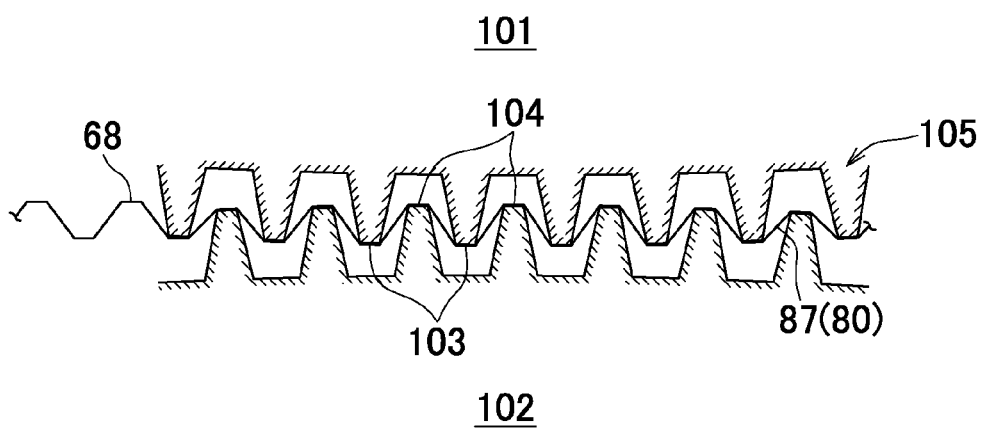

DISPOSABLE WEARING ARTICLE

RELATED APPLICATIONS

The present application is a National Phase of International Application Number PCT/JP2013/058915, filed Mar. 27, 2013, which claims priority to Japanese Application No. 2013-047366, filed Mar. 8, 2013, and Japanese Application No. 2012-077889, filed Mar. 29, 2012.

TECHNICAL FIELD

The present invention relates to disposable wearing articles and, more specifically, to disposable wearing articles such as pant-type disposable diapers, disposable toilet-training pants and disposable incontinent pants each provided with waist elastics.

BACKGROUND

Conventionally, disposable wearing articles provided with waist elastics are known. For example, JP 2008-508082 A (PTL 1) discloses a pull-on wearing article having an absorbent main body and an annular elastic belt including a front belt segment and a rear belt segment, and formed with a waist-opening and a pair of leg-openings wherein the rear belt segment has a length in a longitudinal direction larger than that of the front belt segment. JP 2011-98052 A (PTL 2) discloses a disposable wearing article including an absorbent structure extending across a crotch region into front and rear waist regions and provided along lateral edges thereof with a plurality of thread, strand or string elastics and front and rear waist panels provided with a plurality of thread, strand or string waist elastics extending in a transverse direction in front and rear waist regions, respectively.

CITATION LIST

Patent Literature

{PTL 1}: JP 2008-508082 A
{PTL 2}: JP 2011-98052 A

SUMMARY

Technical Problem

In PTL 1, the disclosed pull-on wearing article is adapted to ensure a comfortable fit on the front side of the wearer and to cover the wearer's buttocks on the rear belt side. However, the pull-on wearing article disclosed in PTL 1 is arranged so that the lateral peripheries of the respective leg-openings provided with the leg elastics rise so as to be put in line contact with the wearer's thighs. With such an arrangement, during use of the article, the lateral peripheries of the respective leg-openings might collapse on the inner side of the pull-on wearing article and might cause body exudates to leak out. In consequence, it is difficult for this pull-on wearing article to cover the wearer's buttocks so as to prevent body exudates from leaking out. In addition, while it is possible for the rear belt segment to cover the wearer's buttocks, it is difficult to prevent exposure of the buttocks perfectly and reliably.

In the disposable wearing article according to the disclosure of PTL 2, the elastic cuffs including the leg elastics are attached, in the front waist region, to the lateral edges of the absorbent structure in a state of being laid inward as viewed in the transverse direction and, in the rear waist region, these elastic cuffs are attached to the rear waist panel in a state of being laid outwardly as viewed in the transverse direction. With such an arrangement, body exudates unlikely to leak out of the front waist region due to contraction of the elastic cuffs and the waist elastics and, in the rear waist region, a distance between the paired elastic cuffs may be maintained sufficiently large to prevent the width dimension of the absorbent structure from being unacceptably constricted to expose a wide range of the wearer's buttocks.

However, the elastic cuffs are secured to the absorbent structure in the rear waist region in a state of being laid outwardly in the transverse direction, so that the width dimension of the crotch region may be gradually enlarged. As a result, when the front and rear waist regions are pulled up, the rear side of the crotch region may not be sufficiently pulled up and a gap might develop between the wearers body and the crotch region, causing the leakage of body exudates. If it is tried to pull up the rear side of the crotch region forcibly, the leg-openings' peripheries might be caught in the wearer's posterior rugae and the buttocks might be partially exposed externally.

An object of the present invention is to provide a disposable wearing article adapted to prevent the buttocks from being exposed externally during use of the article and to ensure a desired fit of the leg-openings' peripheries to the wearers body to prevent leakage of body exudates.

Solution to Problem

There is provided a disposable wearing article having a longitudinal direction and a transverse direction, including: a front waist region; a rear waist region; a crotch region extending between the front and rear waist regions; an annular elastic waist panel including a front waist panel and a rear waist panel joined to each other so as to define the front and rear waist region; a crotch panel joined to the elastic waist panel so as to define the crotch region; an absorbent structure joined to the front and rear waist panels and the crotch panel; and a pair of leg-openings' peripheries lying on both sides in the transverse direction of the crotch region. In a state that the wearing article is flatly developed after the front and rear waist panels have been disjoined from each other, the front and rear waist panels have inner end edges and outer end edges respectively spaced apart from and opposed to each other in the longitudinal direction and extending in the transverse direction, and the inner end edges of the front and rear waist panels lie closer to the crotch region than the outer end edges of the front and rear waist panels, and the inner end edges of the front and rear waist panels cooperate with lateral edges of the crotch panel extending in the longitudinal direction to define the pair of leg-openings' peripheries. In this regard, as used herein, the phrase "in a state that the disposable diaper is flat developed" means the state in which the front and rear waist panels and the crotch panel constituting the disposable diaper has been flatly developed against the elasticity of the elastics.

The wearing article according to one or more embodiments of the present invention further include the following features:

the crotch panel has a pair of leg sheets extending in the longitudinal direction along the lateral edges of the absorbent structure;

the pair of the leg sheets respectively have inner regions adjoining to the absorbent structure and extending in the longitudinal direction and outer regions adjoining to the absorbent structure on the opposite sides to the inner regions and extending in the longitudinal direction;

in a state that the front and rear waist panels are joined to each other, the inner regions rise along the lateral edges of the absorbent structure in a thickness direction of the absorbent structure and the outer regions are bent outwardly in the transverse direction to define the leg-openings' peripheries.

In the wearing article according to one or more embodiments of the present invention, the pair of leg sheets are elasticized leg sheets provided with a plurality of leg elastics, the outer regions of the respective leg sheets are elastic regions in which the plurality of leg elastics are contractibly attached under tension so as to extend in the longitudinal direction, the inner regions are inelastic region provided with none of the elastics, the inner regions rise along the lateral edges of the absorbent structure in a thickness direction of the absorbent structure and the elastic regions are bent outwardly in the transverse direction so as to define the leg-openings' peripheries.

In the wearing article according to another embodiment of the present invention, the pair of leg sheets is elasticized leg sheets provided with leg elastics extending on the lateral edges of the absorbent article and being elastically stretchable and contractible. In a state that the front and rear waist panel is disjoined and the article is flatly developed, an effective elongation dimension of the elasticized leg sheets at the maximum elongation point is larger than a distance dimension in the longitudinal direction from the inner end edge of the front waist region to the inner end edge of the rear waist region and, in consequence, joint regions between the elasticized leg sheets and the crotch panel are formed with a plurality of gathers extending in the transverse direction. As used herein, the term "at the maximum elongation point" means a state in which the article is stretched until gathers/creases/wrinkles due to the contractile force of the elastics are visually disappeared.

Advantageous Effects of Invention

According to one or more embodiments of the present invention, the outer regions of the respective leg sheets bent outwardly of the wearing article so as to define the leg-openings' peripheries are put in surface contact with the wearer's thighs and buttocks with a good fit, and the wearer's buttocks should not be exposed during use thereof. In addition, the leg-openings' peripheries are kept in surface contact with the wearer's body with a good fit and, in consequence, the leakage of body exudates may be reliably prevented. Further, the outer regions of the leg sheets are always in an outwardly bending state, whereby the leg-openings' peripheries should not collapse onto the interior side of the wearing article and should not cause the leakage of body exudates.

According to one or more embodiments of the present invention, the effective elongation dimension at the maximum elongation point of the pair of leg elastic sheets attached to the opposite lateral edges of the crotch panel is larger than the distance dimension in the longitudinal direction from the inner end edge of the front waist region to the inner end edge of the rear waist region, resulting in that the peripheries of the leg-openings are stretched circumferentially along the wearer's thighs and put in close contact with the wearer's thighs. The leg-openings' peripheries are appropriately stretched along with the circumferential dimension of the individual wearers' thighs in this manner and the midsection of the crotch region should not be spaced away from the wearer's body. Thus, it is possible to prevent reliably body exudates from leaking sideways. In addition, the leg-openings' peripheries should not be wedged in the wearer's posterior rugae during use of the wearing article and the wearer's buttocks should not be exposed externally.

BRIEF DESCRIPTION OF DRAWINGS

FIG. 18 (a) is a schematic diagram another example of the manufacturing apparatus for the crotch panel and FIG. 18 (b) illustrates a state of continuous composite sheet in the step of manufacturing the crotch panel.

FIG. 19 is a diagram illustrating a pair of gear rolls being engaged with each other to form gathers in a step of forming gathers of the manufacturing apparatus.

DESCRIPTION OF EMBODIMENTS

First Embodiment

Figure 1:
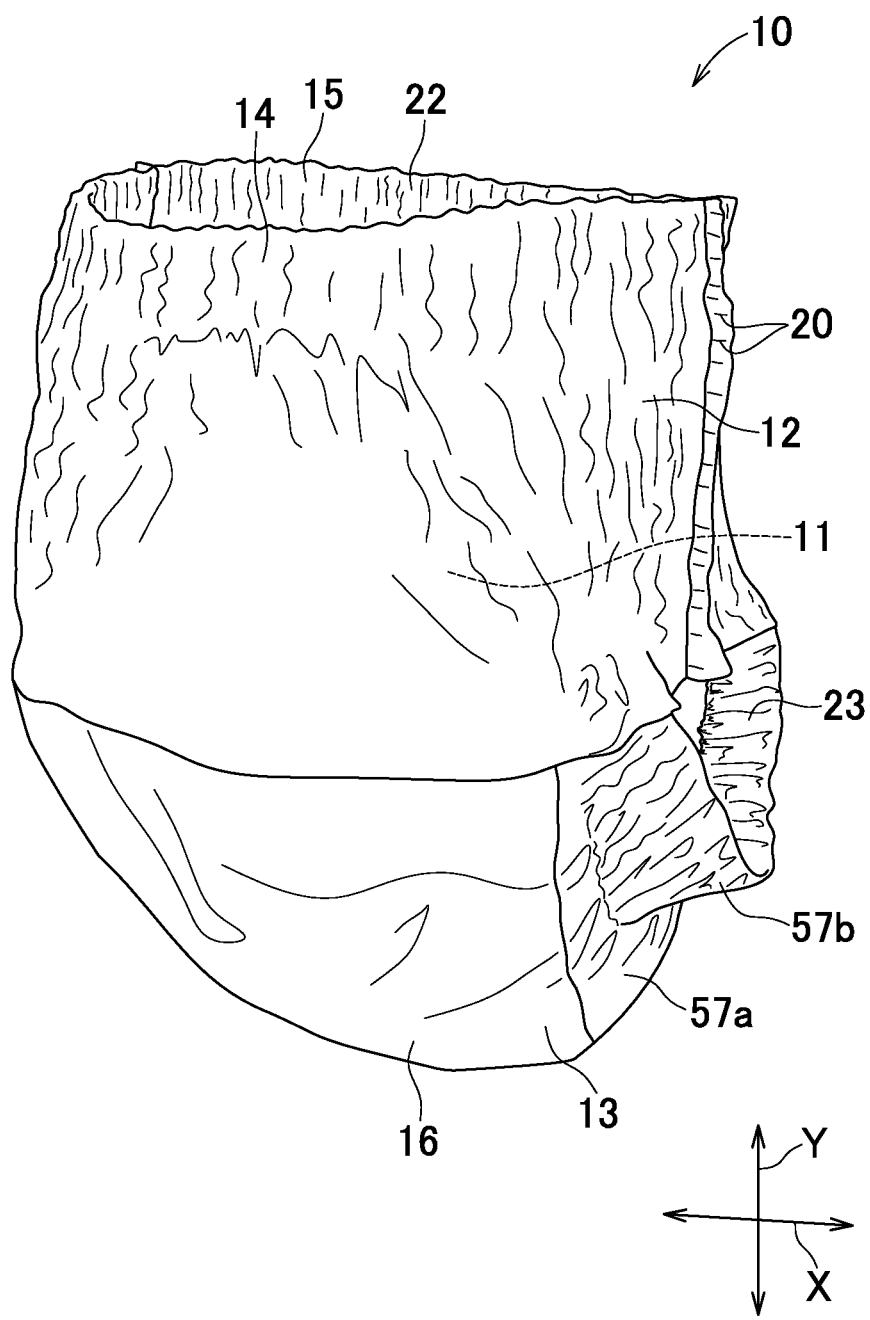
FIG. 1 is a perspective view exemplifying a disposable diaper as an example of a disposable wearing article according to a first embodiment according to the present invention.
Figure 2:
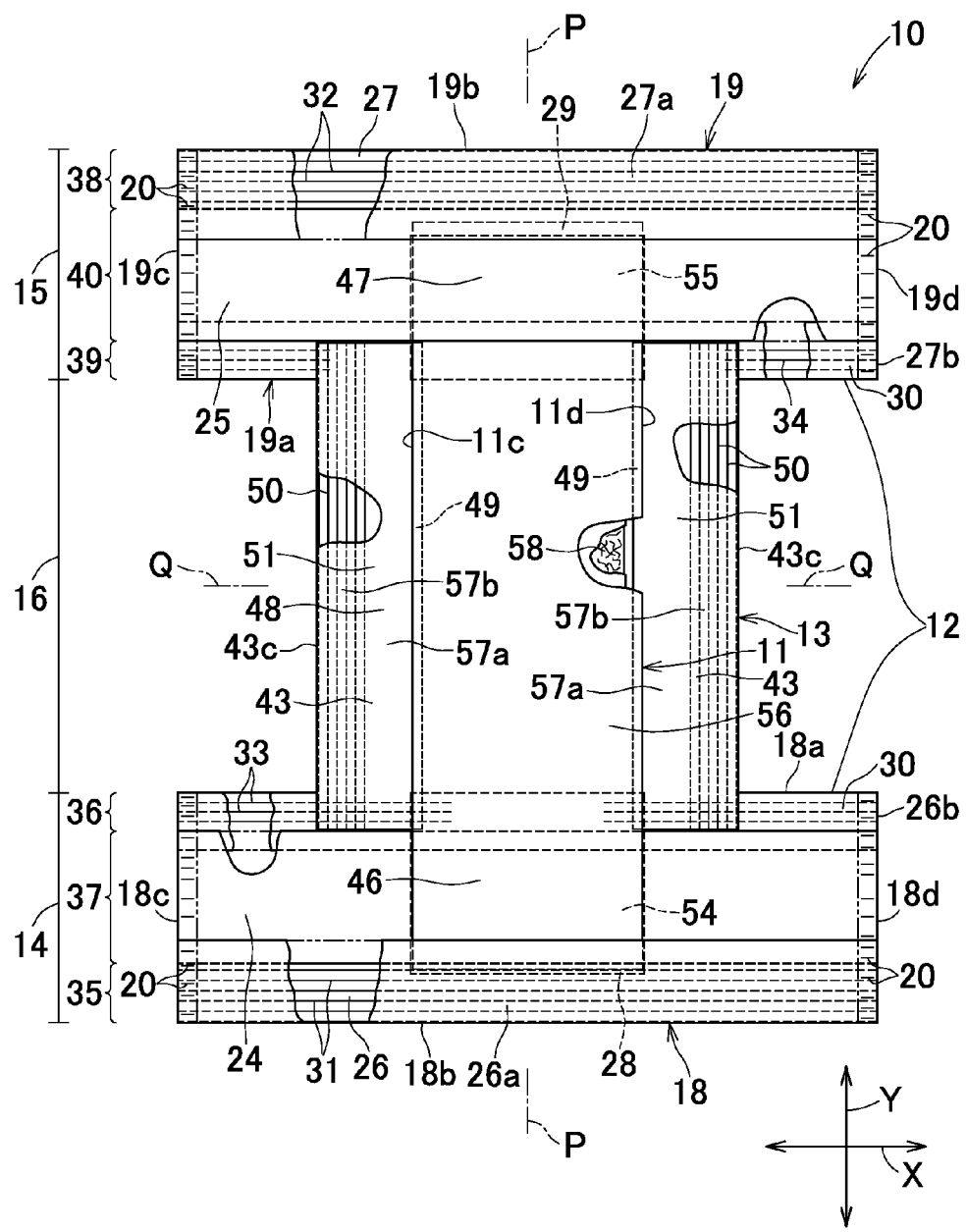
FIG. 2 is a partially cutaway developed plan view illustrating the diaper flatly extended in a longitudinal direction and a transverse direction after front and rear waist panels have been disjoined from each other.
Figure 3:
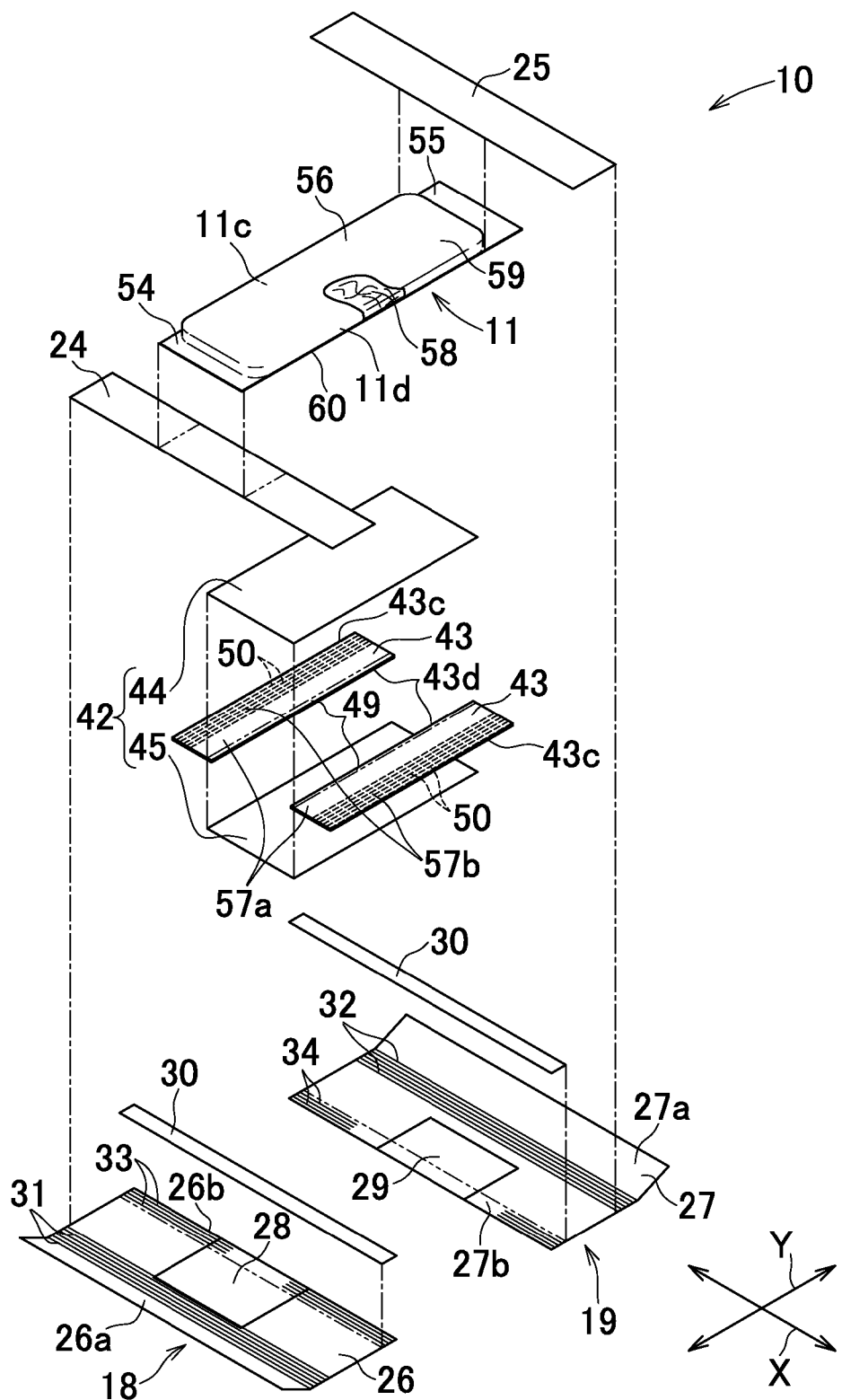
FIG. 3 is an exploded perspective view of the diaper.

Referring to FIGS. 1 through 3, a disposable diaper 10 includes a longitudinal axis P-P, a transverse axis Q-Q, a longitudinal direction Y, a transverse direction X, a body-facing surface to be faced to the wearer's skin, a non-body-facing surface opposite to the body-facing surface, an annular elastic waist panel 12 circumferentially extending about a wearer's waist, an absorbent structure 11 joined to the body-facing surface of the elastic waist panel 12, and an elastic crotch panel 13 attached to the body-facing surface of the elastic waist panel 12. The diaper 10 further includes a front waist region 14, a rear waist region 15 and a crotch region 16 extending between the front and rear waist regions 14, 15 and is symmetrically about the longitudinal axis P-P. In this regard, the front and rear waist regions 14, 15 and the crotch region 16 are sometimes used synonymously with front and rear waist panels 18, 19 and a crotch panel 13 in the specification of the present invention.

The elastic waist panel 12 functions as an elastic belt adapted to stably put the absorbent structure 11 on a crotch region of the wearer and includes a front waist panel 18 defining the front waist region 14 and a rear waist panel 19 defining the rear waist region 15. The front waist panel 18 has a transversely elongate shape contoured by an inner end edge 18a, an outer end edge 18b each extending in the transverse direction X and opposite lateral edges 18c, 18d each extending between the inner and outer end edges 18a, 18b in the longitudinal direction Y. The rear waist panel 19 also has a transversely elongate shape contoured by an inner end edge 19a, an outer end edge 19b each extending in the transverse direction X and opposite lateral edges 19c, 19d each extending between the inner and outer end edges 19a, 19b in the longitudinal direction Y. The inner end edges 18a, 19a are located closer to the crotch panel 13 than the outer end edges s 18b, 19b are. The opposite lateral edges 18c, 18d of the front waist panel 18 are put flat with and joined to the associated lateral edges 19c, 19d of the rear waist panel 19 along a pair of series of seams 20 arranged continually in the longitudinal direction Y with well known heat sealing techniques such as heat-embossing/debossing or ultrasonic sealing techniques and thereupon a waist-opening 22 and a pair of leg-openings 23 are defined. A pair of leg-openings 23 are defined by the inner end edges 18a, 19a of the front and rear waist panels 18, 19 and leg elastic sheets 43 included by the crotch panel 13 to be described later.

The front and rear waist panels 18, 19 respectively have interior waist sheets 24, 25 lying on the body-facing surface and exterior waist sheets 26, 27 lying on the non-body-facing surface. The exterior waist sheets 26, 27 respectively have width dimensions in the longitudinal direction Y larger than those of the interior waist sheets 24, 25 and extend outwardly in the longitudinal direction Y beyond inner and outer end edges of the respective interior waist sheets 24, 25.

As the exterior waist sheets 26, 27, an SMS (spun bonded/melt blown/spun bonded) fibrous nonwoven fabric, a spun bonded fibrous nonwoven fabric, an air-through fibrous nonwoven fabric, a breathable plastic sheet or a laminate sheet of one of the above-mentioned fibrous nonwoven fabrics and the plastic sheet, each having a mass per unit area in a range of about 15 to about 30 g/m$^2$ may be used. The interior waist sheets 24, 25 and the exterior waist sheets 26, 27 may be respectively joined to each other with hot melt adhesive applied to at least one of facing surfaces of the respective pair of the interior and exterior waist sheets or by other heat-sealing techniques.

As material of the interior waist sheets 24, 25, an elastic fibrous nonwoven fabric may be employed and, for example, an elastic fibrous nonwoven fabric of well known art such as a spun bonded fibrous nonwoven fabric, a melt blown fibrous nonwoven fabric, a heat-rolled fibrous nonwoven fabric, an SMS fibrous nonwoven fabric, an air-laid fibrous nonwoven fabric or an air-through fibrous nonwoven fabric may be used alone or in combination to form these interior waist sheets 24, 25. The elastic nonwoven fabric may be formed of, for example, polyethylene- or, polyurethane-based elastomer resin, or a thermoplastic resin made of polyethylene, polypropylene, polyester or acryl. While it is also possible to use an inelastic fibrous nonwoven fabric as a material of the interior waist sheets 24, 25, the interior waist sheet 25 in the rear waist region 14 is adapted to come in direct contact with the wearer's body as will be described later in detail and, for this reason, at least the interior waist sheet 25 may preferably be formed of the elastic fibrous nonwoven fabric to improve flexibility and comfortable texture.

Referring to FIGS. 2 and 3, in middle zones in the transverse direction X of the front and rear waist regions 14, 15, two pieces of a graphic display film 28, 29 made of plastic material and printed the respective non-body-facing surfaces thereof with graphics (not shown) being visually recognizable from outside of the diaper 10 are interposed between the interior waist sheets 24, 25 and the exterior waist sheets 26, 27, respectively. Extension portions of the exterior waist sheets 26, 27 extending in the longitudinal direction Y beyond the outer end edges of the interior waist sheets 24, 25 are folded inwardly to form folded portions 26a, 27a and first and second thread, strand or string elastics 31, 32 are contractibly attached under tension in the respective folded portions 26a, 27a with a hot melt adhesive. Extension portions 26b, 27b extending in the longitudinal direction Y beyond the inner end edges of the interior waist sheets 24, 25 are respectively provided with transversely elongate affixing sheets 30 formed of a fibrous nonwoven fabric and overlapping with the associated extension portions 26b, 27b. Between the affixing sheets 30 and the associated extension portions 26b, 27b, thread, strand or string third and fourth elastics 33, 34 are contractibly attached under tension with hot melt adhesive.

The front waist region 14 has an outer end portion 35 provided with the first elastics 31, inner end portion 36 provided with the third elastics 33 and an intermediate portion 37 extending between the outer and inner end portions 35, 36. The rear waist region 15 has an outer end portion 38 provided with the second elastics 32, an inner end portion 39 provided with the fourth elastics 34 and an intermediate portion 40 extending between the outer and inner end portions 38, 39. The intermediate portions 37, 40 provided with none of the respective elastics are provided with the elastic interior waist sheets 24, 25. In consequence, during use of the diaper 10, the outer end portions 35, 38 as well as the inner end portions 36, 39 of the front and rear waist regions 14, 15 stably fit the wearer's body and the intermediate portions 37, 40 also fit the wearer's body under the contractile force of the interior waist sheets 24, 25. Thus, the diaper 10 should not noticeably displaced on the wearer's body, and body exudates should not leak out of the diaper 10.

The crotch panel 13 included in the crotch region 16 has a base sheet 42 lying in a midsection in the transverse direction X and a pair of elasticized leg elastic sheets 43 prepared separately of the crotch panel 13 and attached to the body-facing surface of the base sheet 42 along joint regions 49 thereof defined by opposite lateral portions of the base sheet 42 coated with hot melt adhesive. Each of the elasticized leg sheets 43 has an inelastic region 57a in which none of elastics is arranged and an elastic region 57b lying immediately outboardly of the inelastic region 57a in the transverse direction X in which a plurality of leg elastics 50 is contractibly attached to leg sheet 43 under tension. In this regard, the elasticized leg sheets 43 will be described as the leg elastic sheets 43. The base sheet 42 is composed of an interior crotch sheet 44 lying on the side of the body-facing surface and an exterior crotch sheet 45 lying on the side of the non-body-facing surface. As material of these interior and exterior crotch sheets 44, 45, well known various types of fibrous nonwoven fabrics or breathable plastic films may be used, but the interior crotch sheet 44 may preferably be formed of a leakage-barrier breathable plastic film considering that this interior crotch sheet 44 is located so as to face the absorbent structure 11 and the exterior crotch sheet 45 may preferably be formed of a fibrous nonwoven fabric having a texture more comfortable than that of a plastic film considering that this exterior crotch sheet 45 constitute part of an outer surface of the diaper 10.

The crotch panel 13 has front and rear end portions 46, 47 and an intermediate portion 48 extending between the front and rear end portions 46, 47. The front and rear end portions 46, 47 are attached to the body-facing surface in vicinities of the inner end edges 18a, 19b of the front and rear waist panels 18, 19 in joining zones defined on the non-body-facing surface of these panels 18, 19 by hot melt adhesive applied to these zones. As a material of the first through fourth waist elastics 31, 32, 33, 34, for example, elastic threads, strands or strings having a fineness in a range of 470 to 780 dtex may be employed and attached to the waist regions 14, 15 at an elongation ratio in a range of 2.0 to 3.5 to the relaxed ones. As a material of the leg elastics 50, elastic threads, strands or strings having a fineness in a range of 310 to 780 dtex may be used and these are attached to the cover sheet 51 at an elongation ratio in a range of 2.0 to 3.5 to the relaxed ones. In addition to these elastics, as material of the respective elastics, a sheet-like elastic material made, for example, of urethane having a predetermined width and thickness may be used.

The absorbent structure 11 has a longitudinally longer pad-like shape and includes front and rear end portions 54, 55, an intermediate portion 56 and an absorbent core 58 extending at least across the crotch region, a body-side liner 59 lying on the side of the body-facing surface of the absorbent core 58 and a wrapping sheet 60 lying on the side of the non-body-facing surface of the absorbent core 58. Almost whole area of the non-body-facing surface of the absorbent structure 11 is coated with a hot melt adhesive in a well known pattern. The front and rear end portions 54, 55 are secured to the body-facing surfaces of the front and rear waist panels 18, 19 with a hot melt adhesive and the intermediate portion 56 is secured to the body-facing surface of the crotch panel 13 with this hot melt adhesive. Referring to FIG. 3, the front end portion 54 of the absorbent structure 11 is secured to the body-facing surface of the interior waist sheet 24 of the front waist panel 18, the rear end portion 55 lies between the interior waist sheet 25 and the exterior waist sheet 27 of the rear waist panel 19 and secured to the body-facing surface of the exterior waist sheet 27. The front end portion 54 of the absorbent structure 11 is secured to the body-facing surface of the interior waist sheet 24 and, in consequence, the elastic and relatively flexible interior waist sheet 24 comes in direct contact with the wearer's skin. Thus the texture may be improved. The rear end portion 55 is secured between the interior waist sheet 25 and the exterior waist sheet 27 and, in consequence, it is possible to prevent body exudates from coming in direct contact with the wearer's body even if body exudates diffuse beyond the crotch region 16 to the portion of the absorbent structure 11 located in the rear waist region 15.

The absorbent core 58 has a mass per unit area in a range of 400 to 600 g/m$^2$ and is composed of a mixture of fluff wood pulp and superabsorbent polymer particles (SAP), optionally added thermally weldable staple fibers and a liquid-permeable fibrous nonwoven fabric. As a material of the body-side liner 59, various types of well known fibrous nonwoven fabrics having a mass per unit area in a range of about 10 to about 30 g/m$^2$ such as a spun bonded nonwoven fabric or an SMS nonwoven fabric may be used. As a material of the wrapping sheet 60, for example, a liquid-impermeable spun bonded nonwoven fabric, an SMS nonwoven fabric, a breathable plastic sheet of a laminate sheet of fibrous nonwoven fabric and plastic sheet each having a mass per unit area in a range of about 10 to about 30 g/m$^2$ may be used. Though not illustrated, it is also possible to implement the present invention in a manner that the body-side liner 59 and the wrapping sheet 60 respectively have extension portions extending outwardly in the transverse direction X beyond the opposite lateral edges of the liquid-absorbent core 58 and a plurality of thread, strand or string elastics are contractibly attached under tension to these extension portions so that, during use of the diaper 10, cuffs spacing away from the body-side liner 59 toward the wearer's crotch may be formed.

Figure 4:
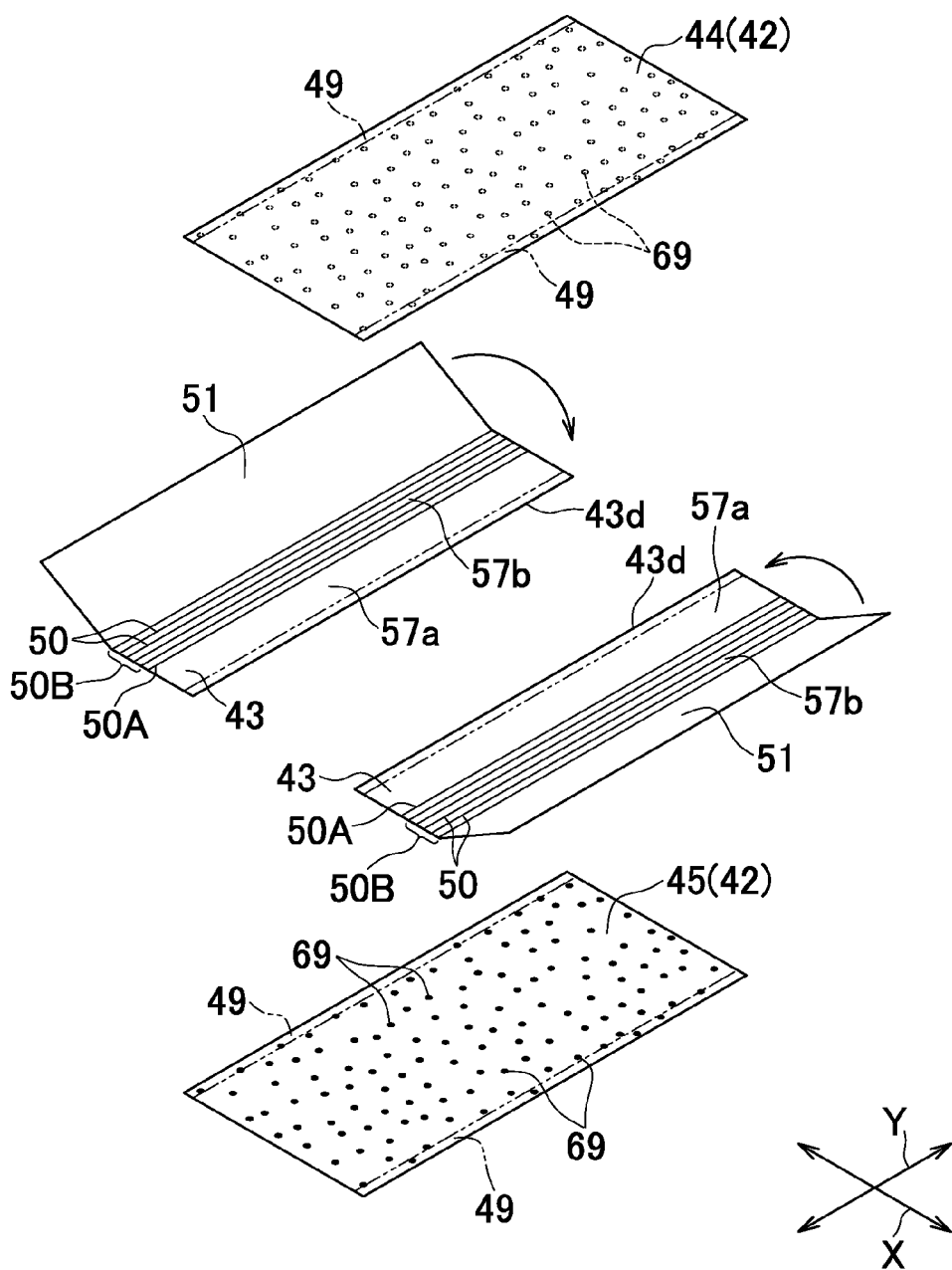
FIG. 4 is an exploded perspective view of a crotch panel.

Referring to FIGS. 2 through 4, the respective leg elastic sheets 43 include leg sheet outer lateral edges 43c and leg sheet inner lateral edges 43d spaced apart from and opposed to each other in the transverse direction X and extending in the longitudinal direction Y, a plurality of thread, strand or string leg elastics 50 and cover sheets 51 to cover these leg elastics 50 wherein each of the leg elastic sheets 43 includes an inelastic region 57a defined on the side of the inner lateral edge 43d in which none of the leg elastics 50 is provided and an elastic region 57b defined on the side of the leg sheet outer lateral edge 43c in which a plurality of leg elastics 50 are provided. In this regard, the term "inner regions" used in Claims correspond to the inelastic regions 57a and the term "outer regions" used in Claims correspond to the elastic regions 57b. Each of cover sheets 51 made of a fibrous nonwoven fabric or a breathable plastic sheet is doubled up and the leg elastics 50 are contractibly attached between two layers of the double up cover sheet 51 with a hot melt adhesive. Inner surfaces of the interior crotch sheet 44 and the exterior crotch sheet 45 constituting the base sheet 42 are fully and at intervals coated with a hot melt adhesive 69 with which the leg sheet inner lateral edges 43d are attached between the interior crotch sheet 44 and the exterior crotch sheet 45 by the joint regions 49. Connection of the leg elastic sheets 43 to the base sheet 42 may be achieved by means of a heat-sealing technique. In this manner, the joint regions 49 in which the leg elastic sheets 43 are joined to the base sheet 42 lie on the side of the leg sheet inner lateral edges 43d and joint of the leg elastic sheets 43 to the base sheets 42 are carried out using hot melt adhesive or heat sealing techniques. As a result, stiffness of the joint regions 49 is sufficiently increased to ensure that, when the main body of the diaper 10 is deformed (e.g., by extension and/or contraction of the first-fourth elastics 31, 32, 33, 34 of the front and rear waist panels 18, 19) or the diaper 10 is expanded to put the diaper 10 on the wearer's body, the force exerted on the leg elastic sheets 43 is appropriately distributed to maintain the state of the leg elastic sheets 43 protruding outwardly in the transverse direction X. In this way, the leg elastic sheets 43 are joined to the lateral edges 11c, 11d of the absorbent structure 11 by the intermediary of the joint regions 49 in a manner such that the inelastic regions 57a adjoin to the absorbent structure 11 and extend in the longitudinal direction Y and the elastic regions 57b adjoin to the inelastic regions 57a outboardly of the inelastic regions 57a as viewed in the transverse direction X and extend in the longitudinal direction Y. Front and rear end portions in the longitudinal direction Y of the respective leg elastic sheets 43 are joined to the inner end edge 18a of the front waist panel 18 and to the inner end edge 19a of the rear waist panel 19, respectively.

Each set of the leg elastics 50 includes a single inner leg elastic 50A lying closest to the associated joint region 49 and one or more outer leg elastics 50B lying outboardly of the inner leg elastic 50A in the transverse direction X, that is, between the associated leg sheet outer lateral edge 43c and the inner leg elastic 50A. The inelastic regions 57a lie between the respective joint regions 49 and the respective inner leg elastics 50A and the elastic regions 57b lie between the respective inner leg elastic 50A and the leg sheet outer lateral edges 43c. Thus, the leg elastics 50 are entirely included in the respective elastic regions 57b. As material of the inner leg elastics 50A and the outer leg elastics 50B, elastic threads, strands or strings having a fineness in a range of about 310 to about 780 dtex may be used with an elongation ratio of about 2.0 to about 3.5.

Figure 5:
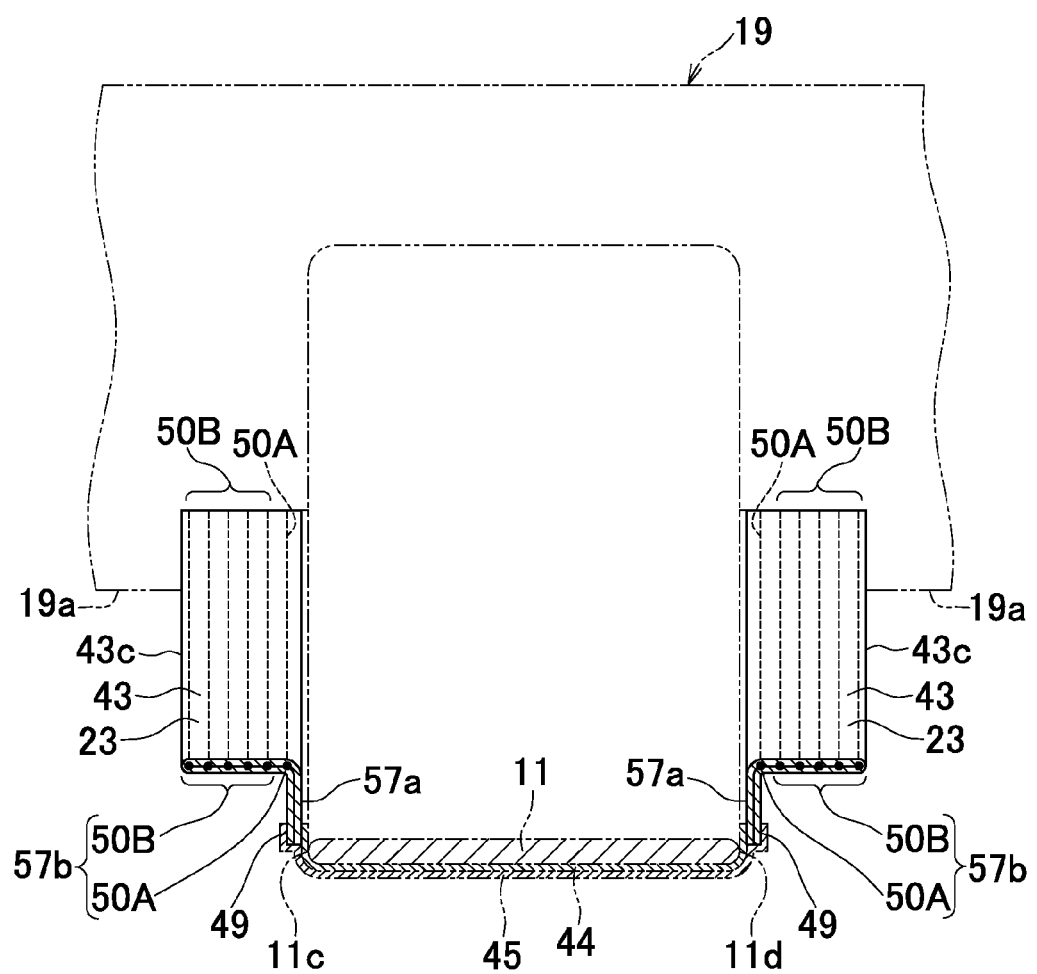
FIG. 5 is a schematic sectional view to illustrate a behavior of leg sheets.

As schematically illustrated in FIG. 5, when the front and rear waist panels 18, 19 are joined to each other, the inelastic regions 57a along the lateral edges 11c, 11d of the absorbent structure 11 rise above the absorbent structure 11 in a thickness direction of the absorbent structure 11 and the elastic regions 57b of the leg elastic sheets 43 are bent outwardly in the transverse direction X to define the leg-openings' peripheries 23. In this regard, FIG. 5 is a schematic sectional view so that the disposable diaper 10 may be seen from the front side and the behavior of the leg elastic sheets 43 may be understood. In FIG. 5, only the leg elastic sheets 43 are indicated by solid lines and the other elements are simplified and indicated by imaginary lines.

As has previously been described, the leg elastic sheets 43 are joined to the lateral edges 11c, 11d of the absorbent structure 11 and the front and rear end portions of the respective leg elastic sheets 43 are joined to the inner end edges 18a, 19a of the front and rear waist panels 18, 19. Assuming that none of the leg elastics 50 is placed, the leg elastic sheets 43 will extend outwardly in the transverse direction X beyond the lateral edges 11c, 11d of the absorbent structure 11 and the leg elastic sheets 43 will be in a state being slung between the front and rear waist panels 18, 19, and the lowest surface of the respective leg elastic sheets 43 will lie at a level substantially corresponding to the bottom surface of the absorbent structure 11 (not shown).

When the single inner leg elastic 50A extending in parallel to one of the lateral edges 11c, 11d of the absorbent structure 11 is contractibly attached under tension to the leg elastic sheets 43, the inelastic region 57a in the leg elastic sheets 43 is moved up from the absorbent structure 11 toward the front and rear waist panels 18, 19. As a result, the inelastic region 57a rises above the absorbent structure 11 as illustrated in FIG. 5. In addition, a plurality of outer leg elastics 50B may be provided between the inner leg elastic 50A and the leg sheet outer lateral edge 43c to ensure that the elastic regions 57b lying between the leg sheet outer lateral edge 43c and the inner leg elastic 50A are moved upwardly toward the front and rear waist panels 18, 19 substantially to a level of the inner leg elastic 50A. In this way, the elastic regions 57b are bent in the transverse direction so as to define the leg-openings' peripheries 23.

With such an arrangement, even when the diaper 10 is free from any external force, for example, when the diaper 10 is in a natural state immediately after it has been taken out from a package in order to use the diaper 10, the elastic regions 57b in the leg elastic sheets 43 are in a state that the elastic regions 57b are bent outwardly in the transverse direction X. As has previously been described, in the pull-on wearing article (diaper) of prior art, for example, disclosed in PTL 1, the lateral edge portions of the leg-openings (corresponding to the leg-openings' peripheries 23 according to the present invention) may be already in a state of collapsing inwardly of the pull-on wearing article or the lateral edge portions of the leg-openings may be collapsed onto the inner side of the pull-on wearing article during use of the article, causing leakage of body exudates. Therefore, in the conventional pull-on wearing article, it is required immediately after the article has been taken out from the package or immediately after the pull-on wearing article has been put on the wearer's body to confirm that the lateral edge portions of the leg-openings are not in the state of collapsing onto the inner side of the pull-on wearing article. In contrast, in the diaper 10 according to the present embodiment, the elastic regions 57b in the leg elastic sheets 43 are always in the state of bending outwardly and therefore it is not required after the diaper 10 has been put on the wearers body to confirm that the leg-openings' peripheries 23 are not in the state of collapsing inwardly. In addition, the leg-openings' peripheries 23 should not collapse and should not cause leakage of body exudates. The elastic regions 57b in the leg elastic sheets 43 are always in the state of bending outwardly and, in consequence, even during use of the diaper 10, the elastic regions 57b are stably kept in surface contact with the wearer's thighs with a good fit, reliably preventing leakage of body exudates. Additionally, a pair of the inelastic regions 57a rising along the lateral edges 11c, 11d of the absorbent structure 11 serve to prevent body exudates from leaking even if a space adapted to collect body waste is formed.

On the basis of the lateral edges 11c, 11d of the absorbent structure 11 in the disposable diaper 10 flatly developed, a dimension of the portion of the respective leg elastic sheets 43 extending from the respective joint regions 49 to the respective inner leg elastics 50A, in other words, a dimension of the respective inelastic regions 57a is typically in a range of 10 mm to 25 mm and a dimension from the respective inner leg elastics 50A to the leg sheet outer lateral edge 43c, namely, a dimension of the respective elastic regions 57b is typically in a range of 20 mm to 35 mm. If the dimension of the respective inelastic regions 57a is less than 10 mm, the contraction of the inner leg elastics 50A will be difficult due to the stiffness of the absorbent structure 11 and it will be difficult for the inelastic regions 57a to rise above the absorbent structure 11. In addition, the contraction of the inner leg elastics 50A will become uneven and it will become difficult for the respective elastic regions 57b to maintain the state of bending outwardly. If the dimension of the respective inelastic regions 57a exceeds 25 mm, it will be apprehended that the inelastic regions 57a might collapse or distorted. If the dimension of the respective elastic regions 57b is less than 20 mm, the length of the elastic regions 57b bending outwardly in the transverse direction X become insufficient to fully cover the wearers buttocks. A dimension of the respective inelastic regions 57a in the transverse direction X may preferably be in a range of 22% to 56% of the dimension of the respective leg elastic sheets 43. The dimension of the respective inelastic regions 57a is less than 22% of the dimension of the respective leg elastic sheets 43, the contraction of the respective inner leg elastics 50A will become difficult under the effect of the stiffness of the absorbent structure 11. In consequence, not only it will become difficult for the respective inelastic regions 57a to rise above the absorbent structure 11 but also the contraction of the respective leg elastics 50A will become uneven and, as a result, it will become difficult for the respective elastic regions 57b to maintain the state of bending outwardly. If the dimension of the respective inelastic regions 57a exceeds 56% of the dimension of the respective leg elastic sheets 43, the inelastic regions 57a might be distorted or collapsed during use of the diaper 10.

According to a variation of the first embodiment, the leg elastic sheets 43 having a relatively long effective elongation dimension may be used. Specifically, it is possible to use the leg elastic sheets 43 having an effective elongation dimension at the point of the maximum elongation being larger than a distance dimension in the longitudinal direction Y from the inner end edge 18a of the front waist panel 18 to the inner end edge 19a of the rear waist panel 19 as measured in the course of stretching the leg elastic sheets 43 in the direction in which the leg elastics extend, and the joint regions between the leg elastic sheets 43 and the crotch panel are formed with a plurality of gathers extending substantially in parallel to each other in the transverse direction X after the front and rear waist panels 18, 19 are disconnected from each other and the disposable diaper 10 is flatly opened. As used herein, the phrase "a distance dimension in the longitudinal direction Y from the inner end edge 18a of the front waist panel 18 to the inner end edge 19a of the rear waist panel 19" means a distance in the longitudinal direction Y from a crossover point between the series of seams 20 arranged in the longitudinal direction Y in the front waist panel 18 and the inner end edge 18a to a crossover point between the series of seams 20 arranged in the longitudinal direction Y in the rear waist panel 19 and the inner end edge 19a. Description of the aspects common to those of the first embodiment will be simplified or omitted hereunder.

Figure 6:
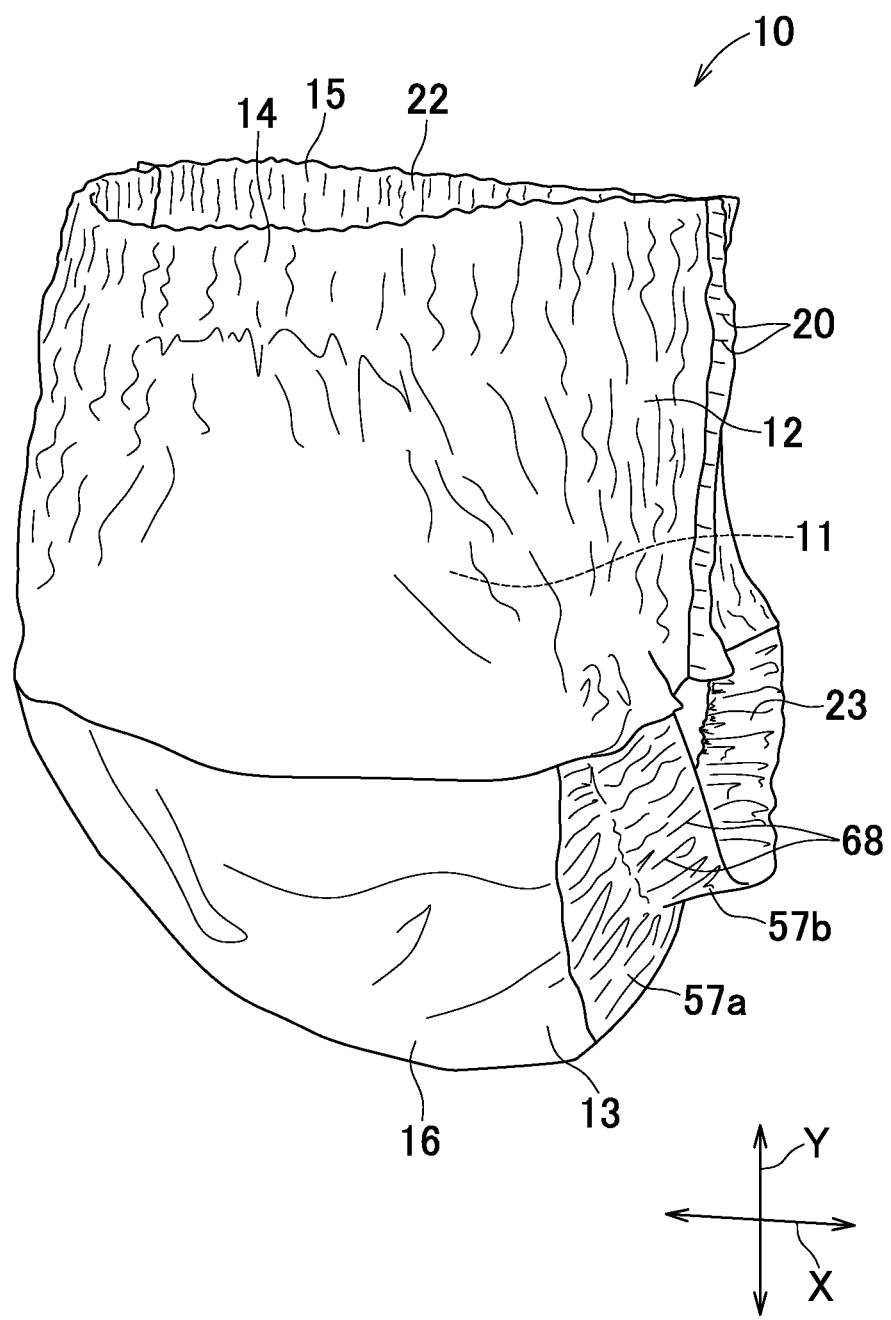
FIG. 6 is a perspective view of a disposable diaper as a variation of the first embodiment.
Figure 7:
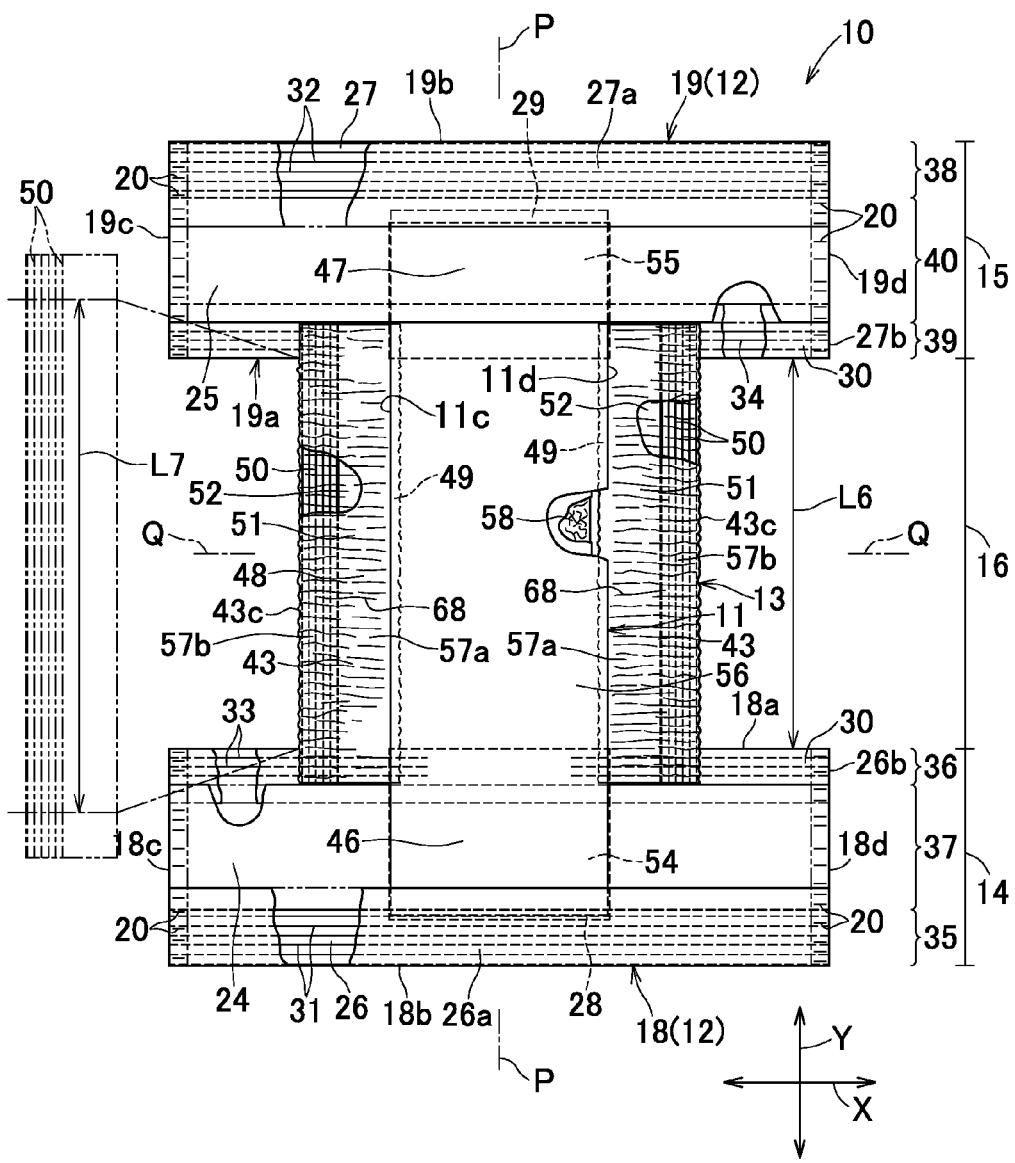
FIG. 7 is a partially cutaway developed plan view of the diaper in a state that respective elastics are stretched to the respective maximum elongation points in a longitudinal direction and in a transverse direction.
Figure 8:
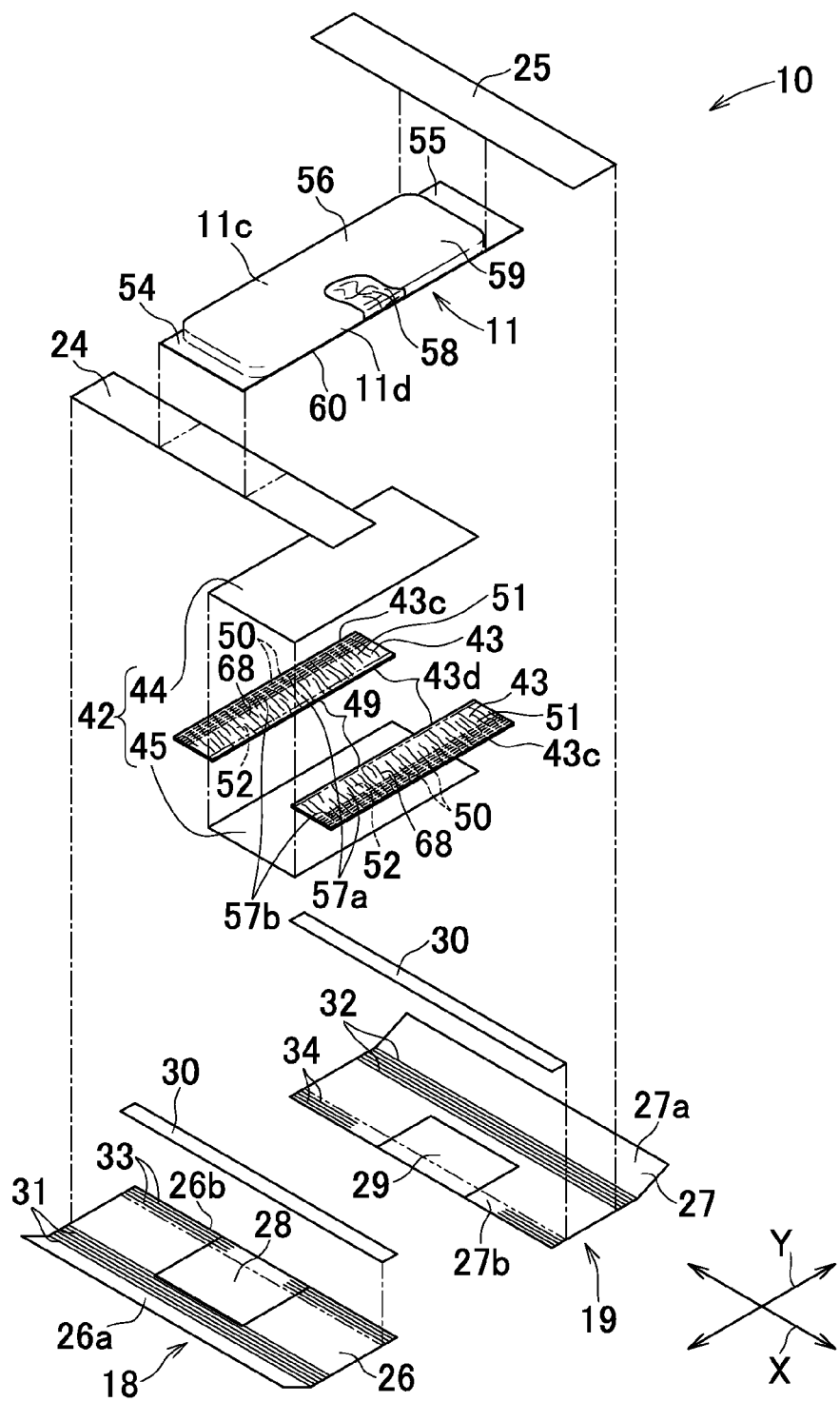
FIG. 8 is an exploded perspective view illustrating another variation of the first embodiment.

Referring to FIGS. 6-8, the disposable diaper 10 includes the annular elastic waist panel 12, the absorbent structure 11 connected to the body-facing surface of the elastic waist panel 12, and the elastic crotch panel 13 attached to the body-facing surface of the elastic waist panel 12. The diaper 10 further includes the front waist region 14, the rear waist region 15 and the crotch region 16 extending between the front and rear waist regions 14, 15. As has previously been described, the elastic waist panel 12 is composed of the front waist panel 18 and the rear waist panel 19. The inner end edges 18a, 19a of the front and rear waist panels 18, 19 cooperate with the leg elastic sheets 43 included in the crotch panel 13 to define a pair of leg-openings' peripheries 23 and the elastic regions 57b in the respective leg elastic sheets 43 are bent outwardly in the transverse direction X.

The front and rear waist panels 18, 19 respectively have interior waist sheets 24, 25 lying on the body-facing surface and exterior waist sheets 26, 27 lying on the non-body-facing surface. The exterior waist sheets 26, 27 are larger than the interior waist sheets 24, 25 in width dimension in the longitudinal direction Y and extend outwardly in the longitudinal direction Y beyond the inner and outer end edges of the interior waist sheet 24. The exterior waist sheets 26, 27 and the interior waist sheets 24, 25 may be manufactured in the manner as has been described. Between the interior waist sheets 24, 25 and the exterior waist sheets 26, 27, graphic display film pieces 28, 29 are interposed. Between opposed surfaces in folded portions 26a, 27a of the exterior waist sheets 26, 27, first and second elastics 31, 32 are contractibly attached under tension. Respective extensions 26b, 27b of the exterior waist sheets 26, 27 are provided with affixing sheets 30 and third and fourth elastics 33, 34 are contractibly attached under tension between the affixing sheets 30 and the respective extensions 26b, 27b.

The front waist region 14 has an outer end portion 35 provided with first elastics 31, an inner end portion 36 provided with third elastics 33 and an intermediate portion 37 defined between the outer and inner end portions 35, 36. The rear waist region 15 has an outer end portion 38 provided with second elastics 32, an inner end portion 39 provided with fourth elastics 34 and an intermediate portion 40 defined between the outer and inner end portions 38, 39. The intermediate portions 37, 40 provided with none of the elastics are provided with the interior waist sheets 24, 25 having elasticity.

The crotch panel 13 forming the crotch region 16 has a base sheet 42 lying in a middle portion in the transverse direction X and the pair of leg elastic sheets 43 attached to the base sheet 42 by the intermediary of the joint regions 49 formed on the body-facing surface of lateral portions of the base sheet 42 coated with a hot melt adhesive. The base sheet 42 is composed of the interior crotch sheet 44 lying on the body-facing surface and the exterior crotch sheet 45 lying on the non-body-facing surface. The crotch panel 13 has the front and rear end portions 46, 47 and the intermediate portion 48 lying between the front and rear end portions 46, 47. The front and rear end portions 46, 47 are attached to the body-facing surface of the inner end edges 18a, 19b of the front and rear waist panels 18, 19 by the intermediary of the joint regions formed on the non-body-facing surface thereof.

The absorbent structure 11 includes front and rear end portions 54, 55, an intermediate portion 56, an absorbent core 58 extending in the longitudinal direction Y at least in the crotch region 16, a body side liner 59 and a cover sheet 60 lying on the non-body-facing surface of the absorbent core 58. The front and rear end portions 54, 55 are attached to the body-facing surface of the front and rear waist panels 18, 19 and the intermediate portion 56 is attached to the body-facing surface of the interior waist sheet 24. The front end 54 of the absorbent structure 11 is attached to the body-facing surface of the interior waist sheet 24 of the front waist panel 18 and, between the interior waist sheet 25 and the exterior waist sheet 27 of the rear waist panel 19, the rear end portion 55 is joined to the body-facing surface of the exterior waist sheet 27. The front and rear end portions 54, 55 of the absorbent structure 11 lie outboardly of the front and rear end portions of the leg elastic sheets 43 as viewed in the longitudinal direction Y and a dimension in the longitudinal direction Y of the leg elastic sheets 43 is smaller than a dimension of the absorbent structure 11 in the longitudinal direction Y. The absorbent core 58 may be manufactured with use of the previously mentioned materials. Though not illustrated, the body side liner 59 and the cover sheet 60 may have respective extensions in the transverse direction X and a plurality of elastics may be contractibly attached to these extensions under tension to form cuffs rising toward the wearer's crotch region.

Referring to FIGS. 7 and 8, the leg elastic sheets 43 has a leg sheet outer lateral edge 43c and a leg sheet inner lateral edge 43d, and includes a plurality of thread, strand or string leg elastics 50, an inelastic region 57a lying on the side of the leg sheet outer lateral edge 43c and adjoining to the absorbent structure 11, and a elastic region 57b lying on the side of the leg sheet outer lateral edge 43c and adjoining to the inelastic region 57a outboardly of the inelastic region 57a as viewed in the transverse direction X. The leg elastics 50 are attached between layers of folded cover sheet 51 with the use of hot melt adhesive (See FIG. 4). Interior and exterior sheets 44, 45 constituting the base sheet 42 respectively have inner surfaces fully coated with hot melt adhesive and the leg sheet inner lateral edge 43d is secured between the interior crotch sheet 44 and the exterior crotch sheet 45 by the intermediary of the joint region 49. In a region of the leg elastic sheets 43 corresponding to the joint region 49, a ribbon-like reinforcing sheet 52 is interposed between doubled over layers of the cover sheet 51 and joined together with hot melt adhesive for the purpose of stably securing the leg elastic sheets 43 to the base sheet 42.

The leg elastics 50 include a single inner leg elastic 50A lying closest to the joint region 49 and one or more outer leg elastics 50B arranged outboardly of the inner leg elastic 50A in the transverse direction X, namely, between the leg sheet outer lateral edge 43c and the inner leg elastic 50A (See FIG. 4). The inelastic region 57a lies between the joint region 49 and the inner leg elastic 50A, and the elastic region 57b lies between the inner leg elastic 50A and the leg sheet outer lateral edge 43c. Thus, the elastic region 57b includes all of the leg elastics 50. As has previously been described, the inelastic region 57a stands up toward the absorbent structure 11 and the elastic region 57b is bent outwardly in the transverse direction X.

According to this embodiment, the respective leg elastic sheets 43 are attached to the body-facing surfaces of the base sheets 42 in a state that the inner end edges 18a, 19b of the front and rear waist panels 18, 19 are contracted from the maximum elongation point, and the leg elastic sheets 43 are formed with a plurality of gathers 68 in the direction intersecting with the direction in which the leg elastics 50 extend. In other words, a plurality of gathers/creases are formed in the transverse direction X. As a result, stiffness of the leg elastic sheets 43 in the transverse direction X increases and the elastic region 57b may be easily maintained in a flat state. Consequently, when no external force is exerted on the diaper 10, for example, when the diaper 10 is in a natural state immediately after the diaper 10 has been taken out from the package to use the diaper 10, the elastic region 57b is planarly bent outwardly in the transverse direction X so that the leg-openings' peripheries 23 may be easily formed. In addition, the respective leg elastic sheets 43 are attached to the base sheet 42 in the state being contracted from the maximum elongation point. In consequence, an elongation ratio of the leg elastics is lower than the case in which the respective leg sheets under tension are joined to the base sheet 42. The elongation ratio of the leg elastics kept at a relatively low level in this manner advantageously prevents the elastic region 57b from rising up (upwardly from the crotch region 16 toward the front and rear waist regions 14, 15). As a result, the elastic region 57b is facilitated to bend outwardly in the transverse direction X. When the diaper 10 has been put on the wearer's body, the elastic region 57a is stably maintained in surface-contact with the wearer's thighs and leakage of body exudates may be reliably prevented. In this way, it is unnecessary to check whether the leg-openings' peripheries have collapsed inward or not after the diaper 10 has been put on the wearer's body.

Referring to FIG. 7, a dimension in the longitudinal direction Y of the crotch region 16, i.e., a distance dimension L6 in the longitudinal direction Y between the inner end edge 18a of the front waist panel 18 and the inner end edge 19a of the rear waist panel 19 is in a range of 205 to 270 mm and an effective elongation dimension L7 of the leg elastic sheets 43 is in a range 225 to 380 mm at the point of the maximum elongation. As used herein, the terms "effective elongation dimension L7" means a dimension a dimension of the portion of the leg elastic sheets 43 attached to the front and rear waist panels 18, 19 lying between the inner end edge 18a of the front waist panel 18 and the inner end edge 19a of the rear waist panel 19 and stretched at the point of the maximum elongation in the longitudinal direction Y. The leg elastic sheets 43 may be elastically elongated at least by 1.05 times or more, preferably by 1.05-1.5 times, more preferably by 1.1-1.4 times of the dimension L6 in the longitudinal direction Y of the crotch region. A dimension ratio of the effective elongation dimension L7 of the leg elastic sheet 43 included in the diaper 10 as a product to the dimension L6 in the longitudinal direction Y of the crotch region may be calculated with use of a test piece composed of the leg elastic sheet 43 joined to the lateral edge of the base sheet 42 in the crotch region 16 being cut out together with the base sheet 42. More specifically, test pieces each having an arbitrary length (e.g., 10 cm) in the longitudinal direction Y are cut out inclusively of the joint regions 49 from the base sheet 42 and the leg elastic sheet 43 in the regions adjoining to the joint regions 49 extending in the longitudinal direction Y in the crotch region 16 of the diaper 10 so that each of these test pieces may have a rectangular shape. Then, regions of the sheet members constituting the base sheet 42 and the leg elastic sheet 43 (i.e., the interior crotch sheet 44, the exterior crotch sheet 45 and cover sheet 51) adjoining to the joint regions 49 are cut into a predetermined width (e.g., 5 mm) to prepare additional test pieces and a dimension of the respective test pieces in the longitudinal direction Y is measured. For the reason that the leg elastic sheets 43 are bonded in a contracted state to the lateral edge of the base sheet 42, the dimension of the sheet member (i.e., the cover sheet 51) constituting the leg elastic sheets 43 is larger than the dimension of the sheet member (i.e., the interior crotch sheet 44 and the exterior crotch sheet 45) constituting the base sheet 42. Based on such dimensional difference, the dimensional ratio of the effective elongation dimension L7 of the leg elastic sheets 43 to the dimension L6 in the longitudinal direction Y of the crotch region may be calculated. In this regard, it should be noted here that the sheet member constituting the base sheet 42 and the leg elastic sheets 43 cut out in this manner as the test pieces should not include the leg elastics 50.

Generally, when the leg elastics 50 are attached in a elastically stretchable and contractible manner in the diaper 10 having the front and rear waist regions 14, 15 and the crotch region 16 prepared separately of each other, the leg elastics 50 are stretched under influences such as movements of the wearer's thighs and sometimes further stretched and eventually squeezed in the wearer's posterior rugae. However, in the diaper 10 according to this embodiment, the leg elastic sheets 43 is attached in a state contracted from the state of the maximum elongation and therefore the leg elastic sheets 43 may be sufficiently stretched and contracted along the wearer's thighs to ensure stable fit to the thighs. Additionally, the contraction and elongation of the fourth elastics 34 extending in the transverse direction X on the rear waist panel 19 cause the leg elastics 50 to be pulled outwardly in the transverse direction X and whereby the dimension of the rear end 47 of the absorbent structure 11 in the transverse direction X may be enlarged. As a result, the wearer's buttocks should not be exposed externally and the leg-openings' peripheries 23 should not be wedged in the wearer's posterior rugae resulting in partial exposure of the wearer's buttocks. As has previously been mentioned, the elastic region partially constituting the leg-openings' peripheries 23 is bent in the transverse direction X toward the outside of the diaper 10 and whereby the elastic region 57b is kept in planar contact with the wearer's thighs with stable fit. In this way, leakage of body exudates may be reliably prevented. In addition, it becomes unnecessary to check, after the diaper 10 has been put on the wearer's body, whether the leg-openings' peripheries 23 have collapsed to the inside or not.

While the first embodiment has been described on the basis of the example in which the leg elastic sheets 43 prepared separately of the base sheet 42 is used, it is possible to form the leg elastic sheets 43 integrally with the base sheet 42.

Second Embodiment

Figure 9:
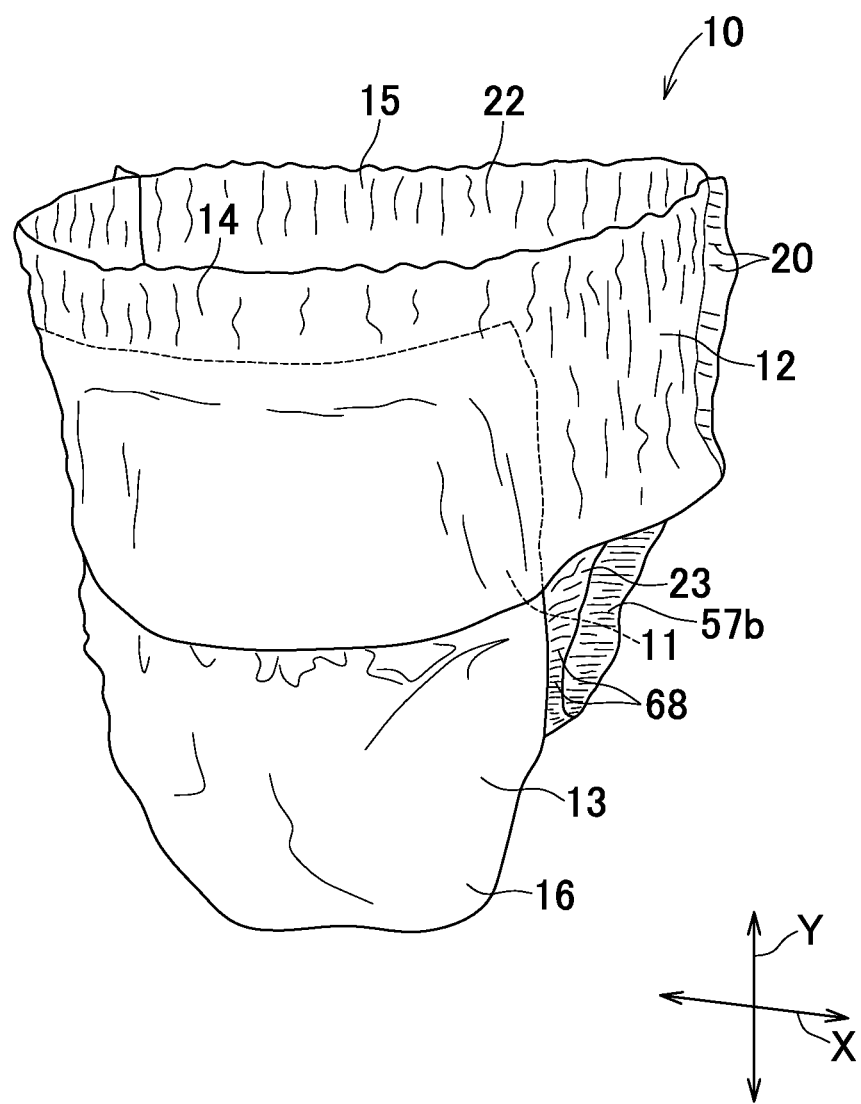
FIG. 9 is a perspective view of a disposable diaper as an example of a disposable wearing article according to a second embodiment.
Figure 10:
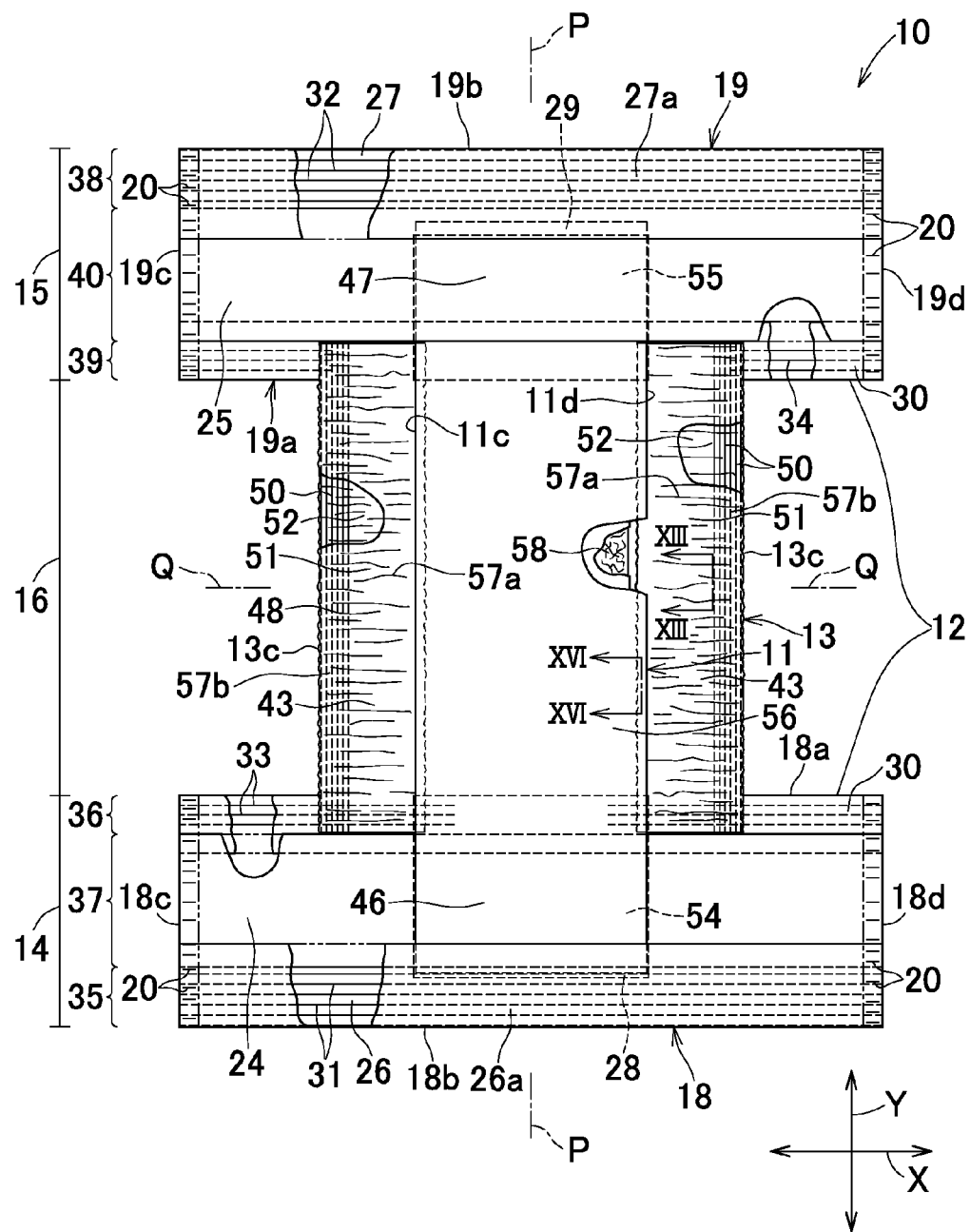
FIG. 10 is a partially cutaway developed plan view of the diaper in a state that respective elastics are stretched to the respective maximum elongation points in the longitudinal direction and in the transverse direction.
Figure 11:
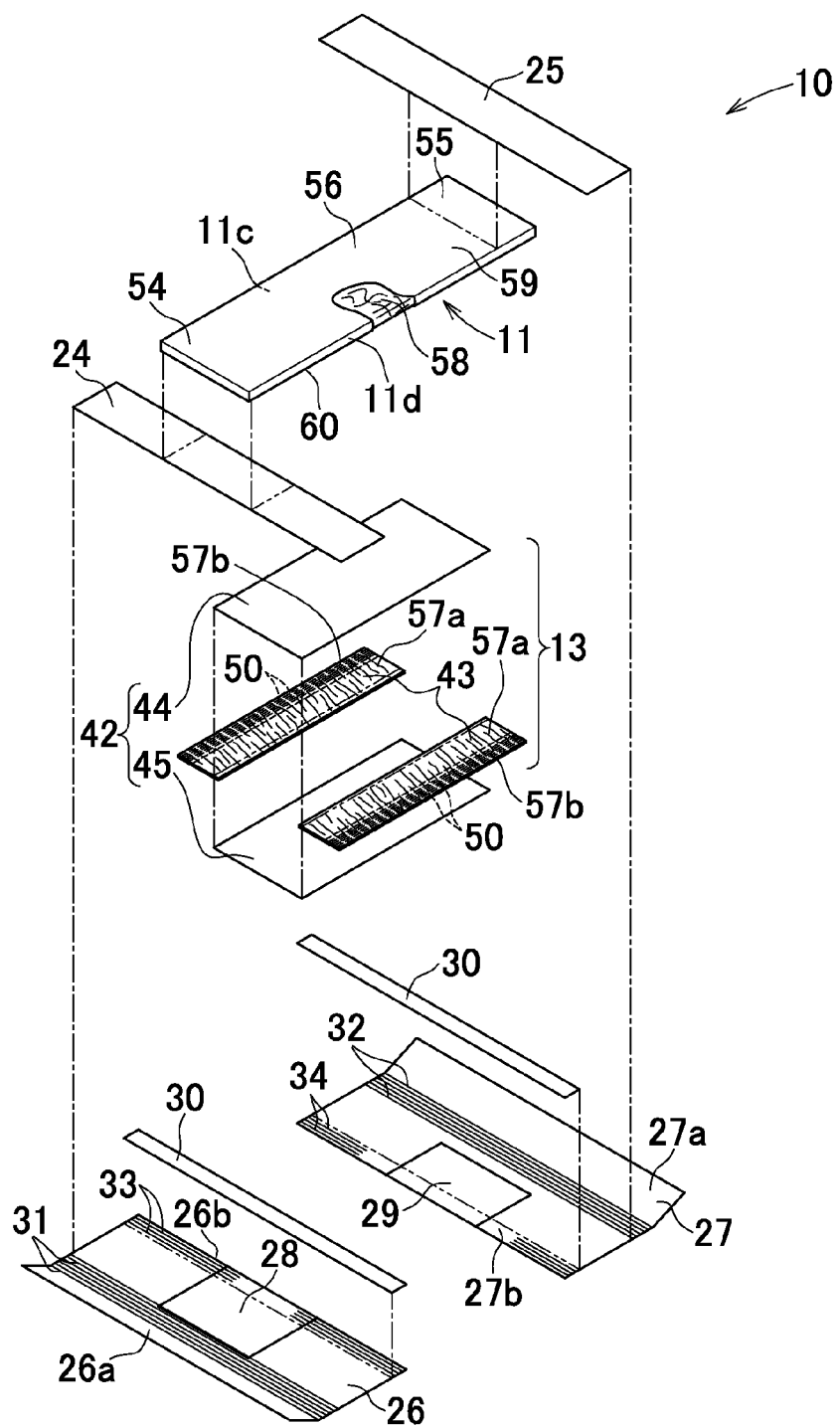
FIG. 11 is an exploded perspective view of the diaper.
Figure 12:
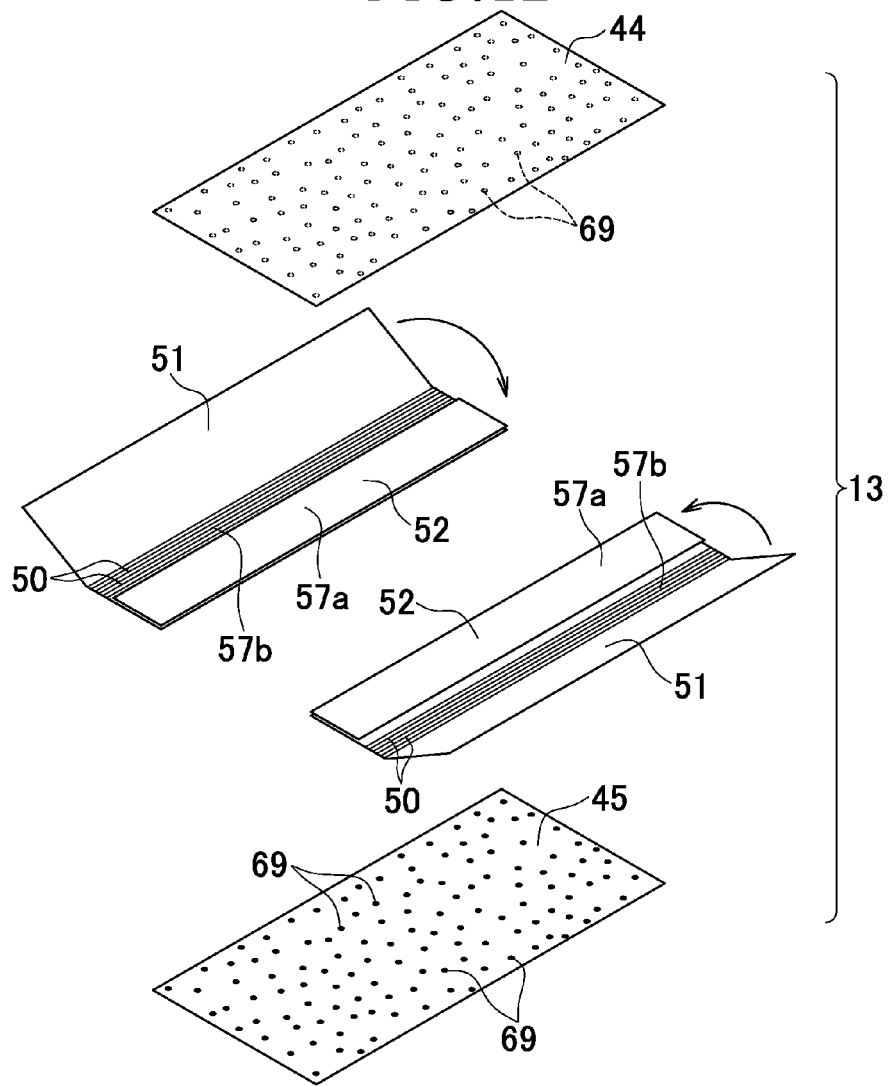
FIG. 12 is an exploded perspective view of leg elastic sheet.

Referring to FIGS. 9 through 11, a disposable diaper 10 has a longitudinal axis P-P and a transverse axis Q-Q, a longitudinal direction Y, a transverse direction X and includes a body-facing surface, a non-body-facing surface opposite to the body-facing surface, an annular elastic waist panel 12 circumferentially extending about a wearer's waist, an absorbent structure 11 joined to the body-facing surface of the elastic waist panel 12, and an elastic crotch panel 13 attached to the body-facing surface of the elastic waist panel 12. The diaper 10 further includes a front waist region 14, a rear waist region 15 and a crotch region 16 extending between the front and rear waist regions 14, 15 and is symmetrically about the longitudinal axis P-P.

The elastic waist panel 12 functions as an elastic belt adapted to stably put the absorbent structure 11 on a crotch region of the wearer and includes a front waist panel 18 defining the front waist region 14 and a rear waist panel 19 defining the rear waist region 15. The front waist panel 18 has a transversely elongate shape contoured by an inner end edge 18a, an outer end edge 18b and opposite lateral edges 18c, 18d extending between the inner and outer end edges 18a, 18b, respectively. The rear waist panel 19 also has a transversely elongate shape contoured by an inner end edge 19a, an outer end edge 19b and opposite lateral edges 19c, 19d extending between the inner and outer end edges 19a, 19b. The opposite lateral edges 18c, 18d of the front waist panel 18 are put flat with and joined to the associated lateral edges 19c, 19d of the rear waist panel 19 along a pair of series of seams 20 arranged continually in the longitudinal direction with well known heat sealing techniques such as heat-embossing/debossing or ultrasonic sealing techniques and thereupon a waist-opening 22 and a pair of leg-openings 23 are defined.

The front and rear waist panels 18, 19 respectively have interior waist sheets 24, 25 lying on the body-facing surface and exterior waist sheets 26, 27 lying on the non-body-facing surface. The exterior waist sheets 26, 27 respectively have width dimensions in the longitudinal direction Y larger than those of the interior waist sheets 24, 25 and extend outwardly in the longitudinal direction Y beyond inner and outer end edges of the respective interior waist sheets 24, 25.

As the exterior waist sheets 26, 27, an SMS (spun bonded/melt blown/spun bonded) fibrous nonwoven fabric, a spun bonded fibrous nonwoven fabric, an air-through fibrous nonwoven fabric, a breathable plastic sheet or a laminate sheet of one of the above-mentioned fibrous nonwoven fabrics and the plastic sheet may be used. The interior waist sheets 24, 25 and the exterior waist sheets 26, 27 may be respectively joined to each other with a hot melt adhesive applied to at least one of facing surfaces of the respective pair of the interior and exterior waist sheets or by the other heat-sealing technique.

As a material of the interior waist sheets 24, 25, an elastic fibrous nonwoven fabric may be employed and, for example, an elastic fibrous nonwoven fabric of well known art such as a spun bonded fibrous nonwoven fabric, a melt blown fibrous nonwoven fabric, a heat-rolled fibrous nonwoven fabric, an SMS fibrous nonwoven fabric, an air-laid fibrous nonwoven fabric or an air-through fibrous nonwoven fabric may be used alone or in combination to form these interior waist sheets 24, 25. The elastic nonwoven fabric may be formed of, for example, polyethylene- or, polyurethane-based elastomer resin, or a thermoplastic resin made of polyethylene, polypropylene, polyester or acryl. While it is also possible to use an inelastic fibrous nonwoven fabric as a material of the interior waist sheets 24, 25, the interior waist sheet 25 in the rear waist region 14 is adapted to come in direct contact with the wearer's body as will be described later in detail and, for this reason, at least the interior waist sheet 25 may preferably be formed of the elastic fibrous nonwoven fabric to improve flexibility and comfortable texture.

Referring to FIGS. 10 and 11, in middle zones in the transverse direction X of the front and rear waist regions 14, 15, two pieces of graphic display film 28, 29 made of plastic material and printed the respective non-body-facing surfaces thereof with graphics (not shown) being visually recognizable from outside of the diaper 10 are interposed between the interior waist sheets 24, 25 and the exterior waist sheets 26, 27, respectively. Extension portions of the exterior waist sheets 26, 27 extending in the longitudinal direction Y beyond the outer end edges of the interior waist sheets 24, 25 are folded inwardly to form folded portions 26a, 27a and first and second thread, strand or string elastics 31, 32 are contractibly attached under tension in the respective folded portions 26a, 27a with a hot melt adhesive. Extension portions 26b, 27b extending in the longitudinal direction Y beyond the inner end edges of the interior waist sheets 24, 25 are respectively provided with transversely elongate affixing sheets 30 formed of a fibrous nonwoven fabric and overlapping with the associated extension portions 26b, 27b. Between the affixing sheets 30 and the associated extension portions 26b, 27b, thread, strand or string third and fourth elastics 33, 34 are contractibly attached under tension with a hot melt adhesive.

The front waist region 14 has an outer end portion 35 provided with the first elastics 31, inner end portion 36 provided with the third elastics 33 and an intermediate portion 37 extending between the outer and inner end portions 35, 36. The rear waist region 15 has an outer end portion 38 provided with the second elastics 32, an inner end portion 39 provided with the fourth elastics 34 and an intermediate portion 40 extending between the outer and inner end portions 38, 39. The intermediate portions 37, 40 provided with none of the respective elastics are provided with the elastic interior waist sheets 24, 25. In consequence, with the diaper 10 put on the wearer's body, the outer end portions 35, 38 as well as the inner end portions 36, 39 of the front and rear waist regions 14, 15 stably fit the wearer's body and the intermediate portions 37, 40 also fit the wearer's body under the contractile force of the interior waist sheets 24, 25. Thus, the diaper 10 should not noticeably displaced on the wearer's body, and body exudates should not leak out of the diaper 10.

The crotch panel 13 has a base sheet 42 lying in a midsection in the transverse direction X and a pair of leg elastic sheets 43. The base sheet 42 is composed of an interior crotch sheet 44 lying on the side of the body-facing surface and an exterior crotch sheet 45 lying on the side of the non-body-facing surface. As a material of these interior and exterior crotch sheets 44, 45, well known various types of fibrous nonwoven fabrics or breathable plastic films but the interior crotch sheet 44 may preferably be formed of a leakage-barrier breathable plastic film considering that this interior crotch sheet 44 is located so as to face the absorbent structure 11 and the exterior crotch sheet 45 may preferably be formed of a fibrous nonwoven fabric having a texture more comfortable than that of a plastic film considering that this exterior crotch sheet 45 constitute part of the outer surface of the diaper 10.

The crotch panel 13 has front and rear end portions 46, 47 and an intermediate portion 48 extending between the front and rear end portions 46, 47. The front and rear end portions 46, 47 are attached to the body-facing surface in vicinities of the inner end edges 18a, 19b of the front and rear waist panels 18, 19 in joining zones defined on the non-body-facing surface of these panels 18, 19 by a hot melt adhesive applied to these zones. As a material of the first through fourth waist elastics 31, 32, 33, 34, for example, elastic threads, strands or strings having a fineness in a range of 470 to 780 dtex may be employed and attached to the waist regions 14, 15 at an elongation ratio in a range of 2.0 to 3.5 to the relaxed ones. As a material of the leg elastics 50 described later in detail, threads, strands or strings having a fineness in a range of 310 to 620 dtex may be employed and attached to the cover sheet 51 at an elongation ratio in a range of 2.0 to 3.0 to the relaxed ones. In addition to these elastics, as a material of the respective elastics, sheet-like elastic material made, for example, of urethane having a predetermined width and thickness may be used.

The absorbent structure 11 has a longitudinally longer pad-like shape and includes front and rear end portions 54, 55, an intermediate portion 56 and an absorbent core 58 extending at least across the crotch region, a body-side liner 59 lying on the side of the body-facing surface of the absorbent core 58 and a wrapping sheet 60 lying on the side of the non-body-facing surface of the absorbent core 58. Almost entire area of the non-body-facing surface of the absorbent structure 11 is coated with a hot melt adhesive in a well known pattern. The front and rear end portions 54, 55 are secured to the body-facing surfaces of the front and rear waist panels 18, 19 with a hot melt adhesive and the intermediate portion 56 is secured to the body-facing surface of the crotch panel 13 with this hot melt adhesive. Referring to FIG. 11, the front end portion 54 of the absorbent structure 11 is secured to the body-facing surface of the interior waist sheet 24 of the front waist panel 18, the rear end portion 55 lies between the interior waist sheet 25 and the exterior waist sheet 27 of the rear waist panel 19 and secured to the body-facing surface of the exterior waist sheet 27. The front end portion 54 of the absorbent structure 11 is secured to the body-facing surface of the interior waist sheet 24 and, in consequence, the elastic and relatively flexible interior waist sheet 24 comes in direct contact with the wearers skin. Thus the texture may be improved. The rear end portion 55 is secured between the interior waist sheet 25 and the exterior waist sheet 27 and, in consequence, it will be possible to prevent body exudates from coming in direct contact with the wearers body even if body exudates diffuse beyond the crotch region 16 to the portion of the absorbent structure 11 located in the rear waist region 15.

The absorbent core 58 has a mass per unit area in a range of 400 to 600 g/m$^2$ and is composed of a mixture of fluff wood pulp and superabsorbent polymer particles (SAP), optionally added thermally weldable staple fibers and a liquid-permeable fibrous nonwoven fabric. As a material of the body-side liner 59, various types of well known fibrous nonwoven fabrics having a mass per unit area in a range of about 10 to about 30 g/m$^2$ such as a spun bonded nonwoven fabric or an SMS nonwoven fabric may be used. As a material of the wrapping sheet 60, for example, a liquid-impermeable spun bonded nonwoven fabric, an SMS nonwoven fabric, a breathable plastic sheet or a laminate sheet of a fibrous nonwoven fabric and a plastic sheet each having a mass per unit area in a range of about 10 to about 30 g/m$^2$ may be used. Though not illustrated, it is also possible to implement the present invention in a manner that the body-side liner 59 and the wrapping sheet 60 respectively have extension portions extending outwardly in the transverse direction X beyond the opposite lateral edges of the liquid-absorbent core 58 and a plurality of thread, strand or string elastics are attached in a stretchable and contractible manner to these extension portions so that, during use of the diaper 10, stand-up cuffs spacing away from the body-side liner 59 toward the wearer's crotch may be formed.

Referring to FIGS. 10 through 13, the respective leg elastic sheets 43 include a plurality of thread, strand or string leg elastics 50 and cover sheets 51 adapted to cover the leg elastics 50. Each of the cover sheets 51 is formed of a single fibrous nonwoven fabric or plastic sheet doubled up to interleave the leg elastics 50 therebetween and is secured together with these interleaved leg elastics 50 with hot melt adhesive so that the leg elastics 50 may be contractibly secured within the doubled up portion. Each of the leg elastic sheets 43 includes the elastic region 57b in which a plurality of leg elastics 50 is provided and the inelastic region 57a in which none of the leg elastics 50 is provided. The leg elastic sheets 43 are attached, in a contracted state in the longitudinal direction Y as a whole, to the body-facing surface of the base sheet 42 located inboard of these leg elastic sheets 43 as viewed in the transverse direction and the front and rear end portions of the crotch panel.

Figure 13:
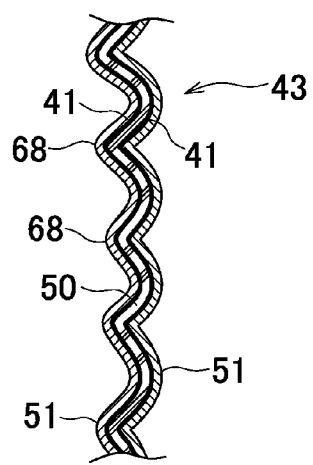
FIG. 13 is a schematic sectional view taken along line XIII-XIII in FIG. 10.

Referring to FIG. 13, the leg elastics 50 are secured within the respective doubled up cover sheets 51 with joint regions 41 formed of a hot melt adhesive applied to entire circumferential surfaces of these leg elastics 50 so that the leg elastic sheets 43 may be undulated in the longitudinal direction Y to form a plurality of gathers 68. In this regard, as long as the leg elastics 50 are attached to the cover sheet 51 in a contracted state, the joint region 41 may be arranged with some intervals in the longitudinal direction Y with regard to the entire circumferential surfaces of the leg elastics 50.

Figure 14:
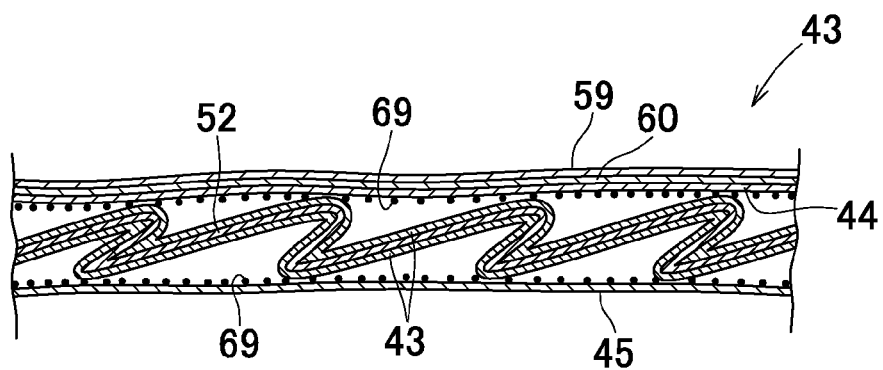
FIG. 14 is a schematic sectional view taken along line XIV-XIV in FIG. 10.

Referring to FIG. 14, the interior waist sheet 44 and the exterior waist sheet 45 cooperating with each other to define the base sheet 42 are coated over entire inner surfaces thereof with a hot melt adhesive 69 with which the inner side portions of the respective leg elastic sheets 43 are secured between the interior waist sheet 44 and the exterior waist sheet 45. In the inner side zones of the respective leg elastic sheets 43 defined inboard of the leg elastics 50 as viewed in the transverse direction X and adapted to be secured to the base sheet 42, a band-like reinforcing sheet 52 is interleaved and secured with a hot melt adhesive within each of the doubled up cover sheets 51 so that the respective leg elastic sheets 43 may be stably secured to the base sheet 42.

Referring to FIG. 14, the inner side portions of the leg elastic sheets 43 are secured, in a state of being neither stretched nor contracted, between the interior and exterior waist sheets 44, 45. In consequence, only the outer side portions of the leg elastic sheets 43 provided with the leg elastics 50 are contractible.

Figure 15:
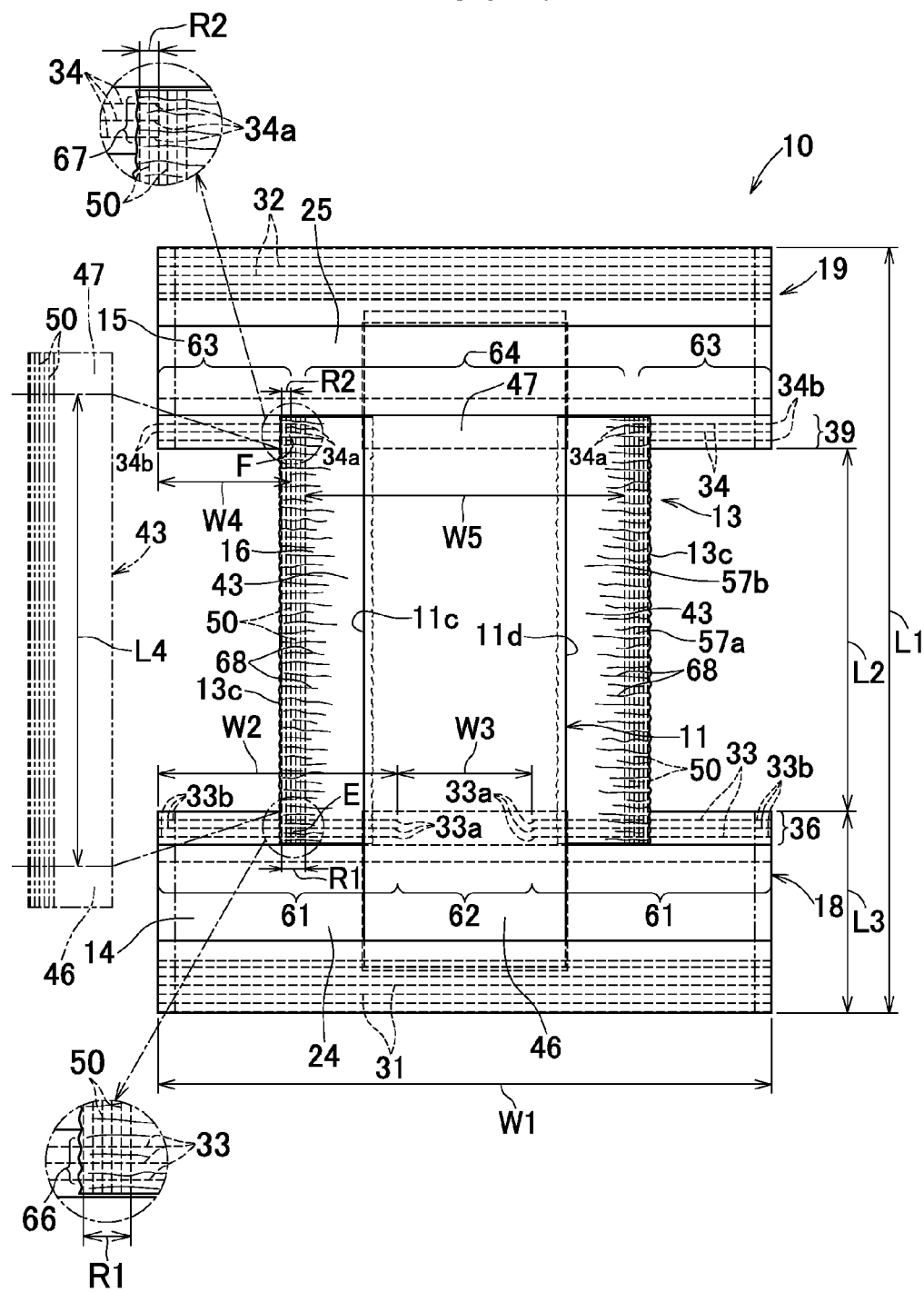
FIG. 15 is a developed plan view similar to FIG. 10, indicating the leg sheets in a stretched state by an imaginary line.

Referring to FIG. 15, a dimension L1 in the longitudinal direction Y of the diaper 10 is in a range of about 450 to about 550 mm, a dimension W1 in the transverse direction X of the diaper 10 is in a range of about 320 to about 380 mm and a dimension L2 in the longitudinal direction Y of the crotch region 16 is in a range of about 200 to about 280 mm A dimension L3 in the longitudinal direction Y of the respective lateral edges 18d of the front waist region 14 (which is the same as a dimension in the longitudinal direction Y of the lateral edges 19d of the rear waist region 15) is in a range of about 100 to about 140 mm.

In the inner end portion 36 of the front waist region 14, first elastic zones 61 in which the third elastics 33 are arranged and a first inelastic zone 62 extending in the transverse direction X between the first elastic zones 61 in which none of the third elastics 33 is arranged are defined. In the inner end portion 39 of the rear waist region 15, second elastic zones 63 in which the fourth elastics 34 are arranged and second inelastic zones 64 extending in the transverse direction X between the second elastic zones 63 in which none of the fourth elastics 34 is arranged are defined. Regarding the dimensions of the respective zones, a dimension W2 in the transverse direction X of the respective first elastic zones 61 is in a range of about 120 to about 140 mm, a dimension W3 in the transverse direction X of the first inelastic zone 62 is in a range of about 60 to about 100 mm, a dimension W4 in the transverse direction X of the respective second elastic zone 63 is in a range of about 60 to about 90 mm and a dimension W5 in the transverse direction X of the second inelastic zone 64 is in a range of about 170 to about 210 mm.

The first inelastic zone 62 may be formed by a method as will be described (the second inelastic zone 64 also may be formed by the same method). For example, the zones of the exterior waist sheet 26 to be formed with the first elastic zones 61 are coated on the inner surface thereof with hot melt adhesive in an appropriate pattern and the continuous third elastics 33 are contractibly fed under tension onto the inner surface of the exterior waist sheet 26 including these zones so that the third elastics 33 may be secured to the adhesive-coated zones. At this state, the third elastics 33 may be cut in the zone to be defined as the first inelastic zone 62 to ensure that the third elastics 33 automatically contract (snap-back) since the segments of the third elastics 33 are not secured to this zone 62 with the adhesive. As a result, the third elastics 33 having a contractile force are substantially not present in the first inelastic zone 62. The terms "substantially not present" suggest that negligibly short segments of the third elastics 33 may sometimes stay behind in the first inelastic zone 62 after the third elastics 33 have been cut in the first inelastic zone 62. The third elastics 33 are preferably cut in a single step so as to snap-back without any segments remaining in the first inelastic zone. Alternatively, it is possible to cut off utterly the segments of the third elastics 33 lying in the first inelastic zone 62 without relying on the snap-back effect.

The method for defining the first and second inelastic zones 62, 64 is not limited to the method as has been described above and these inelastic zones 62, 64 may be defined with use of the other methods. For example, the segments of the third elastics 33 to be laid in the first inelastic zone 62 may be laid under no tension in the first inelastic zone 62. In this case, the first inelastic region 62 may be coated with a hot melt adhesive and the third elastics 33 may be secured under no tension. It is also possible to deprive or inhibit a contractile property of the third elastics 33 laid under tension in the first inelastic zone 62 and thereby making this zone inelastic. As has been described just above, the term "inelastic zones" used herein includes the case in which the third and fourth elastics 33, 34 are substantially not present in the first and second inelastic zones 62, 64 and the case in which the third and fourth elastics 33, 34 are present in these zones but these elastics develop no contractile property.

The third elastics 33 respectively have outer end edges 33b lying on the opposite lateral edges 18c, 18d of the front waist region 14 and inner end edges 33a lying so as to overlap with the absorbent structure 11 wherein these third elastics 33 are secured under tension between the inner and outer end edges. The fourth elastics 34 respectively have outer end edges 34b lying on the opposite lateral edges 19c, 19d of the rear waist region 15 and inner end edges 34a lying so as to overlap the leg elastics 50 wherein these fourth elastics 34 are secured under tension between the inner and outer end edges. Such arrangement of the third and fourth elastics 33, 34 ensures that the absorbent structure 11 may be kept in close contact with the wearer's body in the inner end portion 36 of the front waist region 14 under the effect of a contractile force of the third elastics 33 and a gap inducing leakage of body exudates between the wearer's body and the absorbent structure 11 should not be created even by movements of the wearer's thighs. In the inner end portion 39 of the rear waist region 15, the fourth elastics 34 are not intersecting with the absorbent structure 11 and, in consequence, the contractile force thereof should not be exerted on the absorbent structure 11 and not develop cracks and/or gathers/creases causing leakage of body exudates.

Referring to FIG. 15, the dimension in the longitudinal direction Y of the crotch region 16, i.e., the distance dimension L2 in the longitudinal direction Y between the inner end edge 18a of the front waist region 14 and the inner end edge 19a of the rear waist region 15 is in a range of 200 to 280 mm and an effective elongation dimension L4 at the maximum elongation point of the respective leg elastic sheets 43 is in a range of about 210 to about 420 mm. The terms "effective elongation dimension L4" used herein means a dimension in the longitudinal direction Y of the portion being elastically contractible in the longitudinal direction Y of the respective leg elastic sheets 43 extending between the inner end edge 18a of the front waist region 14 and the inner end edge 19a of the rear waist region 15 except the front and rear end portions 46, 47 which are secured to the front and rear waist regions 14, 15 and substantially neither stretchable nor contractible. In this way, the effective elongation dimension L4 of the respective leg elastic sheets 43 is at least 1.05 or higher, preferably at a ratio in a range of 1.05 to 1.5 and more preferably at a ratio in a range of 1.1 to 1.4 to the dimension L2 in the longitudinal direction Y of the crotch region. In conventional diapers in which the front and rear waist regions and the crotch region are separately prepared and the leg elastics are contractibly attached under tension, an elastic performance required to act on the wearer's body might be insufficient and, as a result, the leg elastics 50 might be pulled inward, for example, due to the movement of the wearer's thighs and wedged in the wearer's posterior rugae. In contrast, in the diaper 10 according to this embodiment, the leg elastic sheets 43 are attached in a contracted state so that the leg elastic sheets 43 are sufficiently stretched along the wearer's thighs to ensure the required elastic performance. In this way, the diaper 10 is stably kept in close contact with the wearer's thighs. In addition, the leg elastics 50 are pulled outwardly under the effect of contraction of the second elastic zones 63 and therefore the dimension in the transverse direction X of the rear end portion 47 of the absorbent structure 11 is not changed or even enlarged in comparison to this dimension before the diaper 10 is put on the wearer's body. Thus, the wearer's buttocks should not be exposed externally.

Referring to an enlarged scale in FIG. 15, a dimension R2 in the transverse direction X of respective second intersection zones 67 between the fourth elastics 34 and the leg elastics 50 in the rear waist region 15 may preferably be in a range of about 10 to about 30% of a total dimension R1 in the transverse direction X of the leg elastics 50 on the respective sides. If this ratio is lower than about 10%, the fourth elastics 34 do not intersect with the leg elastics 50 at all, it will be impossible to form a virtual elastic belt sufficiently pressed against the wearer's thighs to prevent leakage of body exudates and, in consequence, body exudates might leak out. If this ratio is higher than about 30%, the contractile force of the fourth elastics 34 will interfere with the contractile property of the leg elastics 50 and, as a result, the opposite laterals of the absorbent structure 11 will contract so as to reduce the dimension W7 in the transverse direction X of the portion of the crotch region 16 on the side of the rear waist region 15 and, in consequence, the wearer's buttocks might be exposed externally.

Respective first intersection zones 66 in which the third elastics 33 intersect with the leg elastics 50 in the front waist region have a dimension corresponding to the dimension R1 in the transverse direction X of the leg elastics 50 and the dimension R2 in the transverse direction X of the respective second intersections 67 is smaller than the dimension R1 in the transverse direction X of the respective first intersection zones 66 in the transverse direction X.

Of the first and second elastics 61, 63, at least the second elastics 63 preferably have a tensile stress at the maximum elongation point higher than a tensile stress of at the maximum elongation point of the respective elastic zones defined by the leg elastics 50. As has previously been described, the intersection zones between the leg elastics 50 and the fourth elastics 34 are relatively small, the leg elastics 50 are pulled outwardly in the transverse direction X under the effect of the tensile force of the fourth elastics 34 to ensure that the absorbent structure 11 sufficiently cover the wearers buttocks when the front and rear waist regions 14, 15 are pulled up to put the diaper on the wearers body so long as the tensile stress of the second elastics 63 is higher than that of the elastic zones defined by the leg elastics 50. More specifically, the tensile stress of the second elastic zones 63 at the maximum elongation point is in a range of about 3.0 to about 6.5 N/25 mm wide and the tensile stress of the elastic zones defined by the leg elastics 50 at the maximum elongation point is in a range of about 2.0 to about 2.9 N/25 mm wide.

Figure 16:
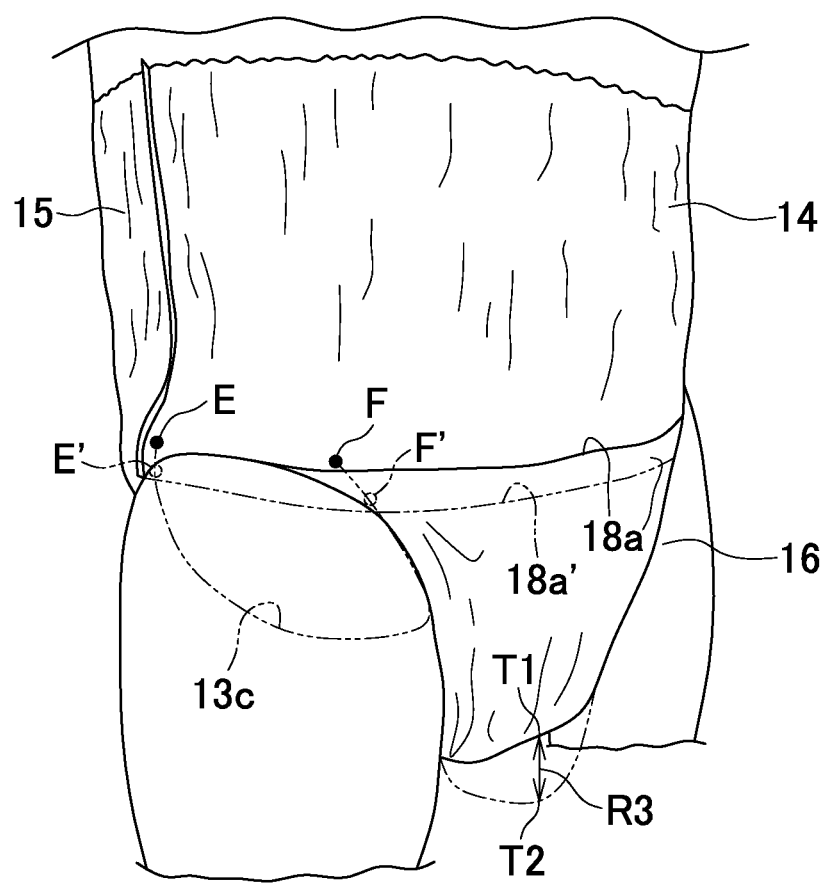
FIG. 16 illustrates the diaper put on the wearer's body.

Referring to FIG. 16, assuming that a dimension L2 in the longitudinal direction Y of the crotch region 16 is smaller than a circumferential dimension of the wearer's thigh, the leg elastic sheets 43 will be stretched along the wearers thighs so that the outer lateral edges 13c of the respective leg elastic sheets 43 may be located along the wearer's groin and the front end portion E and the rear end portion F may be located in vicinities of the wearers ilium. In this situation, a bottom zone T1 of the crotch region 16 is kept in contact with the lowest zone of the wearer's crotch and ensures that body exudates is absorbed and contained by the absorbent structure. In contrast, assuming that the dimension L2 in the longitudinal direction Y of the crotch region 16 is smaller than the circumferential dimension of the wearer's thigh but the leg elastic sheets 43 are attached, in a state elongated to a dimension at the maximum elongation point thereof, to the front and rear waist regions 14, 15, the leg elastic sheets 43 will not be stretched any more from the situation in which the outer lateral edges 43c of the respective leg elastic sheets 43 are in contact with the wearers thighs. As a result, front and rear end portions E', F' will be located at levels lower than the front and rear end portions E, F. In such situation, a bottom zone T2 of the crotch region 16 will be located at a level lower than the bottom zone T1 and a differential dimension in the longitudinal direction Y of these bottom zones T1, T2 will be in a range of about 5 to about 10 mm. If the bottom zone T2 is located in a range of about 5 to about 10 mm lower than the wearer's crotch, the absorbent structure 11 is likely to be spaced apart from the wearer's crotch and causes a problem that body exudates might leak sideways. If the leg elastic sheets 43 already in the maximum elongation state are further pulled up in order to avoid such undesired situation, the peripheries of the respective leg-openings might be wedged in the wearers posterior rugae with appearance of Fundoshi (loin cloth) in back view. Thus, the diaper 10 might be disfigured.

<Process of Manufacturing the Crotch Panel 13>

Figure 17:
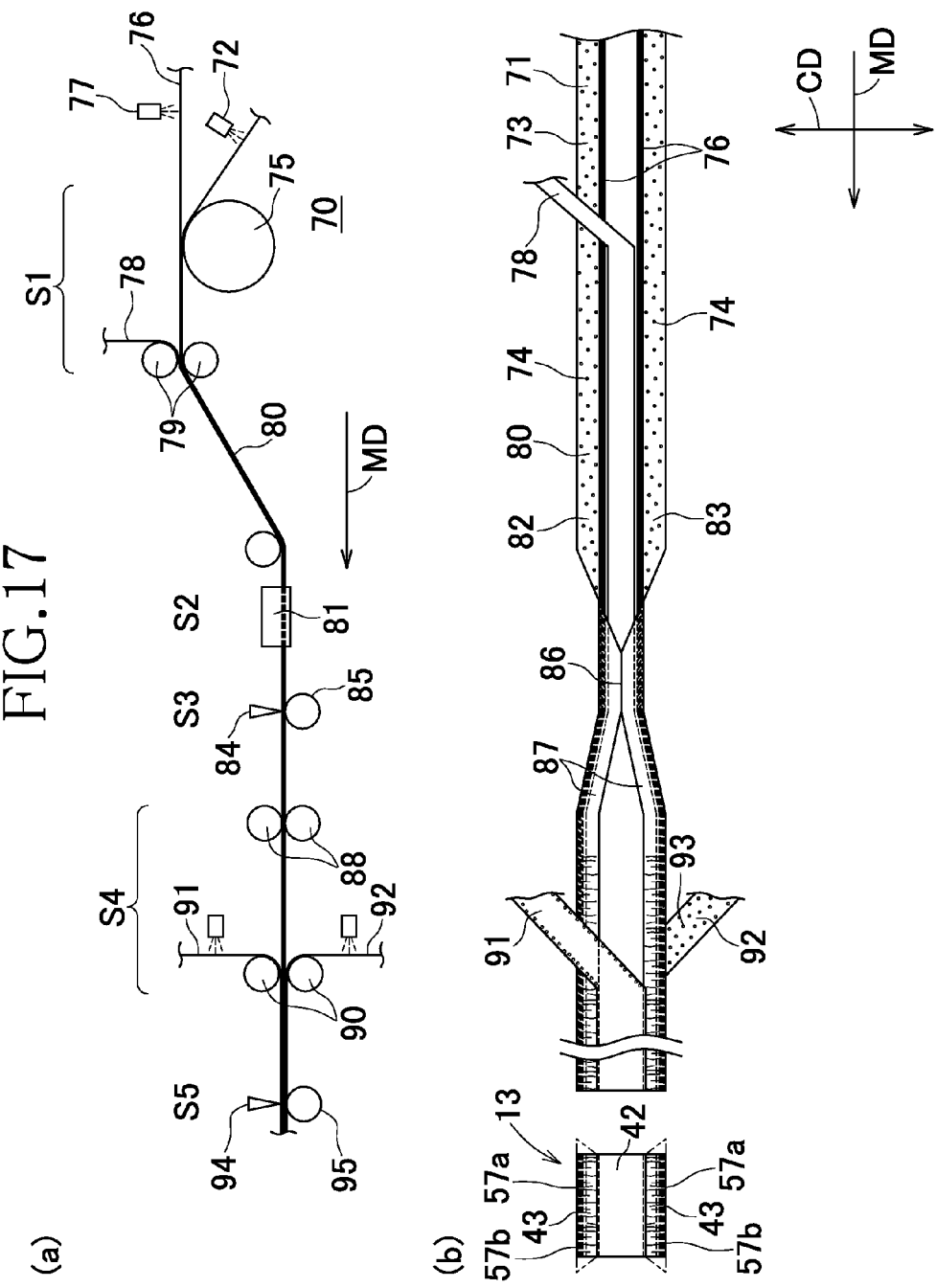
FIG. 17 (a) is a schematic diagram illustrating an example of manufacturing apparatus for the crotch panel and FIG. 17 (b) illustrates a state of continuous composite sheet in the step of manufacturing the crotch panel.

Referring to FIG. 17 (a), an apparatus 70 for manufacturing the crotch panel 13 exemplified herein includes a continuous elastics attachment step S1, a step S2 of folding, a step S3 of cutting, a step S4 of snap-back attachment and a second step S5 of cutting in this order in the machine direction MD. FIG. 17 (b) illustrates states of the continuous composite sheet in the respective steps S1 through S5 in FIG. 17 (a).

<Continuous Elastics Attachment Step S1>

A continuous composite sheet 71 as a base material of the cover sheets 51 is fed from a feed roll and coated by a coater 72 on a first surface 73 along laterals opposite to each other in the cross direction CD with hot melt adhesive. Then the continuous composite sheet 71 is fed to a rotary drum 75 and a pair of continuous elastics 76 as base material of the leg elastics 50 is fed onto the first surface 73 of the continuous composite sheet 71 on the rotary drum 75. The continuous elastics 76 have previously been continuously coated by a coater 77 on the whole circumference thereof in the machine direction MD with a hot melt adhesive and secured to the first surface 73 of the continuous composite sheet 71 with the hot melt adhesive. Then, the continuous composite sheet 71 and a continuous film 78 as a base material of the reinforcing sheet 52 are fed and pressed between a pair of press rolls 79 so as to locate the continuous film 78 between the pair of the continuous elastics 76 on the first surface 73. The surface of the continuous film facing the first surface 73 of the continuous composite sheet 71 has previously been coated with hot melt adhesive and the continuous film 78 is secured to the continuous composite sheet 71 with the adhesive to form continuous composite sheet 80.

<Folding Step S2>

Laterals 82, 83 opposite to each other in the cross direction CD of the continuous composite sheet 80 are folded inwardly by a folding device 81 and the inner surface of each of the folded laterals 82, 83 is joined to itself with hot melt adhesive together with the continuous elastics interposed between the folded inner surfaces.

<First Step S3 of Cutting>

The continuous composite sheet 80 is fed into a gap between a cutter 84 and an anvil roller 85 located so as to face each other and a midsection 86 in the cross direction CD thereof is cut so as to bisect the continuous composite sheet 80 and to form separated regions 87.

<Snap-Back Attachment Step S4>

The continuous composite sheet 80 is fed between a pair of circumferential velocity regulating rolls 88. Then, continuous composite sheets 91, 92 as base materials for the interior waist sheet 44 and the exterior waist sheet 45, respectively, are fed by a pair of feed rolls 90 to the first surface 73 and the surface opposite thereto of the continuous composite sheet 80. The continuous composite sheets 91, 92 have previously been coated along the opposite lateral edges with hot melt adhesive 93 with which the separated regions 87 are secured. A circumferential velocity V1 of the circumferential velocity regulating rolls 88 is higher than a circumferential velocity V2 of the feed rolls 90 and a ratio of the circumferential velocity V1 to the circumferential velocity V2 (i.e., V1/V2× 100) is in a range of about 105 to about 150%, preferably in a range of about 110 to about 140%. In other words, the circumferential velocity regulating rolls 88 rotate at a circumferential velocity in a range of 1.05 to 1.5 times, preferably in a range of 1.1 to 1.4 times of the circumferential velocity V2 of the feed rolls 90. In this way, the separated regions 87 contract between the circumferential velocity regulating rolls 88 and the feed rolls 90 and consequentially the feed rolls 90 are fed with a quantity per unit time (second) of the continuous composite sheet 80 larger than a quantity per unit time (second) thereof fed in the other steps S1 to S3 and the separated regions 87 are attached to the continuous composite sheets 91, 92 in a contracted state.

<Second Cutting Step S5>

The continuous composite sheet 80 is fed between a gap defined between a cutter 94 and an anvil 95 opposite to each other and cut along a cut line extending in the cross direction CD to form a plurality of crotch panels 13. As indicated by imaginary lines, while the portions of the individual crotch panel 13 provided with the leg elastics 50 of the leg elastic sheet 43 would otherwise be in an elongated state, these portions may be contracted under the effect of the circumferential velocity regulating rolls 88 to the dimension corresponding to the length dimension L2 in the longitudinal direction Y of the crotch region 13 before the crotch panel 13 is attached to the elastic waist panel 12.

FIG. 18 (a) is a schematic diagram illustrating another embodiment of the apparatus 70 for manufacturing the crotch panel 13 and including a continuous elastics attachment step S1, a step S2 of folding, a step S3 of cutting, a gather forming step S4, a snap-back attachment step S5 and a second step S6 of cutting in this order as viewed in the machine direction MD. FIG. 18 (b) is a diagram illustrating an appearance of continuous composite sheet in the course of the respective steps S1 through S6 illustrated in FIG. 18 (a).

Of the steps in the manufacturing apparatus according to this embodiment, only one step not included in the manufacturing apparatus illustrated in FIG. 17 (a) and FIG. 17 (b) is the gather forming step S4 and the circumferential velocities of the rolls in the respective steps are uniform. In other words, there is no particular step in which a relatively large amount of the continuous composite sheet is fed. Considering this, only the gather forming step S4 not included in the manufacturing process according the first embodiment will be described hereunder.

<Gather Forming Step S4>

Referring to FIG. 18 (a) and FIG. 19, the gather forming step S4 is carried out by a pair of gear rolls 101, 102 respectively provided on outer peripheral surfaces with a plurality of teeth (gears) 103, 104 extending in the cross direction CD and adapted to be engaged with each other. The respective separated regions 87 of the continuous composite sheet 80 are successively fed into an engagement zone 105 between the respective gear rolls 101, 102 and the separated regions 87 are formed with undulating gathers 68 extending in the cross direction CD (in the transverse direction X of the diaper 10) and repeating folds in the machine direction MD (in the longitudinal direction Y of the diaper 10). Each of teeth 103 of the gear roll 101 has a trapezoidal cross-sectional shape and is the same in shape and in size as each of teeth 104 of the gear roll 102. Teeth tips of the respective teeth 103, 104 are preferably chamfered in order to prevent these teeth tips from breaking the separated regions 87 when these teeth tips crimp the separated regions 87. In this way, the respective separated regions 87 are formed with plural gathers 68 in the gather forming step S4 and, as a result, a length dimension in the machine direction MD of the respective separated regions 87 after having passed the gather forming step S4 is reduced in comparison with a length dimension thereof in a stretched state. In this regard, the present invention is not limited to the method as has been described just above, it is also possible to form the leg elastic sheets 43 integrally with the base sheet 42. Specifically, the composite sheet as the base material of the base sheet 42 fed in the machine direction MD may be gear-stretched along the opposite laterals thereof only and the elastics may arranged along the opposite laterals having been gear-stretched in this manner. In this way, the opposite laterals of the base sheet 42 may be elasticized with the same effect as that obtained by separately arranging the leg elastic sheets 43 according to the aforementioned embodiments of the present invention.

The constituent elements of the disposable diaper 10 are not limited to those described in the description but the other types of materials widely used in the relevant technical field may be used without limitation unless otherwise stated. The terms "first", "second", "third" and "fourth" used in the description and claims of the present invention are used merely to distinguish the similar elements, similar positions or other similar means.

The disclosure described above may be arranged in at least the following features.

A disposable wearing article having a longitudinal direction and a transverse direction, including:
a front waist region;
a rear waist region;
a crotch region extending between the front and rear waist regions;
an annular elastic waist panel including a front waist panel and a rear waist panel joined to each other so as to define the front and rear waist region;
a crotch panel joined to the elastic waist panel so as to define the crotch region;
an absorbent structure joined to the front and rear waist panels and the crotch panel; and
a pair of leg-openings' peripheries lying on both sides in the transverse direction of the crotch region, wherein,
in a state that the wearing article is flatly developed after the front and rear waist panels have been disjoined from each other, the front and rear waist panels have inner end edges and outer end edges respectively spaced apart from and opposed to each other in the longitudinal direction and extending in the transverse direction, the inner end edges of the front and rear waist panels lie closer to the crotch region than the outer end edges of the front and rear waist panels, and
the inner end edges of the front and rear waist panels cooperate with lateral edges of the crotch panel extending in the longitudinal direction to define the pair of leg-openings' peripheries, wherein:
the crotch panel has a pair of leg sheets extending in the longitudinal direction along the lateral edges of the absorbent structure;
the pair of the leg sheets respectively have inner regions adjoining to the absorbent structure and extending in the longitudinal direction and outer regions adjoining to the absorbent structure on the opposite sides to the inner regions and extending in the longitudinal direction;
in a state that the front and rear waist panels are joined to each other, the inner regions rise above the absorbent structure along the lateral edges of the absorbent structure in a thickness direction of the absorbent structure, and the outer regions are bent outwardly in the transverse direction so as to define the leg-openings' peripheries.

The feature disclosed above may include at least the following embodiments, which may be taken in isolation from or in combination with one another.
(1) The leg sheets are prepared separately of the crotch panel.
(2) The leg sheets are elasticized leg sheets provided with a plurality of leg elastics,
the outer regions of the respective leg sheets are elastic regions in which the plurality of the leg elastics are attached under tension so as to extend in the longitudinal direction,
the inner regions are inelastic regions provided with none of the elastics,
the inner regions rise above the absorbent structure along the lateral edges of the absorbent structure in the thickness direction of the absorbent structure, and
the elastic regions are bent outwardly in the transverse direction so as to form the leg-openings' peripheries.
(3) A dimension in the transverse direction of the respective elastic regions is 20 mm or larger and a dimension in the transverse direction of the respective inelastic regions is 10 mm or larger.
(4) The dimension in the transverse direction of the respective inelastic region is in a range of 22% to 56% of a dimension of the respective elasticized leg sheets.

(5) An effective elongation dimension of the elasticized leg sheets at the maximum elongation point is larger than a distance dimension in the longitudinal direction from the inner end edge of the front waist region to the inner end edge of the rear waist region, and the joint regions between the elasticized leg sheets and the crotch panel are formed with a plurality of gathers extending in parallel to each other in the transverse direction.

(6) An effective elongation dimension of the elasticized leg sheets is in a range of about 1.05 to about 1.5 times of the distance dimension in the longitudinal direction from the inner end edge of the front waist region to the inner end edge of the rear waist region.

(7) The elasticized leg sheets respectively include the leg elastics and cover sheets to which the leg elastics are attached,
  the elasticized leg sheets are attached to the inner end edges of the front and rear waist regions in an elastically contracted state and are formed with gathers extending in the transverse direction and repeating folds in the longitudinal direction, and
  the joint regions between the elasticized leg sheets and the crotch panel are formed with a plurality of gathers extending in the transverse direction.

(8) The elasticized leg sheets respectively include the leg elastics and cover sheets to which the leg elastics are attached, and
  the elasticized leg sheets being attached to the inner end edges of the front and rear waist regions in a state of being mechanically formed with gathers extending in the transverse direction of the absorbent structure and repeating the folds in the longitudinal direction.

(9) The front waist region has a pair of first elastic zones extending in the transverse direction along the inner end edge and spaced apart from each other in the transverse direction and a first inelastic zone extending between the first elastic zones;
  the rear waist region has a pair of second elastic zones extending in the transverse direction along the inner end edge and spaced apart from each other in the transverse direction and a second inelastic zone extending between the second elastic zones;
  the leg elastics intersect with the first and second elastic zones and a dimension in the transverse direction of the second inelastic zone is larger than a dimension in the transverse direction of the first inelastic zone; and
  a dimension in the transverse direction of respective first intersection zones in which the first elastic zones intersect with the leg elastics is larger than a dimension in the transverse direction of respective second intersection zones in which the second elastic zones intersect with the leg elastics.

(10) A dimension in the transverse direction of the respective second intersection zones in the rear waist region is in a range of about 10 to about 30% of a dimension in the transverse direction of the leg elastics.

(11) The absorbent structure lies in a midsection in the transverse direction of the crotch panel, the first elastic zones extend from opposite lateral edges of the front waist region to the absorbent structure and the second elastic zones extend from opposite lateral edges of the rear waist region to the leg elastics.

(12) A tensile stress at the maximum elongation point of at least the second elastic zones of the first and second elastic zones is higher than a tensile stress at the maximum elongation point of elastic zones defined by the leg elastics.

(13) A dimension in the longitudinal direction of the leg sheets is smaller than a dimension in the longitudinal direction of the absorbent structure.

(14) A dimension in the longitudinal direction of the front waist region is substantially the same as a dimension in the longitudinal direction of the rear waist region and inner end edges of the front and rear waist regions rectilinearly extending in the transverse direction are substantially orthogonal to the leg elastics.

REFERENCE SIGNS LIST

10 disposable wearing article (disposable diaper)
11 absorbent structure
11c, 11d lateral edges of absorbent structure
12 elastic waist panel
13 crotch panel
14 front waist region
15 rear waist region
16 crotch region
18 front waist panel
19 rear waist panel
18a lower end edge of front waist region (inner end edge of front waist panel)
18b upper end edge of front waist region (outer end edge of front waist panel)
18c, 18d lateral edges of the front waist region
19a lower end edge of rear waist region
19b upper end edge of rear waist region
19c, 19d lateral edges of rear waist region
20 seams
23 leg-openings' peripheries
42 base sheet
43 leg elastic sheet
43c outer lateral edge of leg sheet
49 joint region
50 leg elastics
57a inelastic region (inner region)
57b elastic region (outer region)
61 first elastic zone
62 first inelastic zone
63 second elastic zone
64 second inelastic zone
66 first intersection zone
67 second intersection zone
L2 distance dimension in longitudinal direction from inner end edge of front waist region to inner end edge of rear waist region.
L4 effective elongation dimension of leg elastic sheet at maximum elongation point
R1 dimension in transverse direction of first intersection zone
R2 dimension in transverse direction of second intersection zone
W2 dimension in transverse direction of first elastic zone
W3 dimension in transverse direction of first inelastic zone
W4 dimension in transverse direction of second elastic zone
W5 dimension in transverse direction of second inelastic zone
X transverse direction
Y longitudinal direction

The invention claimed is:
1. A disposable wearing article having a longitudinal direction and a transverse direction, said disposable wearing article comprising:
  a front waist region;
  a rear waist region;

a crotch region extending between the front and rear waist regions;

an annular elastic waist panel including a front waist panel and a rear waist panel joined to each other so as to define the front and rear waist regions;

a crotch panel joined to the elastic waist panel so as to define the crotch region;

an absorbent structure joined to the front and rear waist panels and the crotch panel;

a pair of leg sheets extending in the longitudinal direction along lateral edges of the absorbent structure; and a pair of leg-openings lying on both sides in the transverse direction of the crotch region, wherein in a state that the wearing article is flatly developed after the front and rear waist panels have been disjoined from each other, the front and rear waist panels have inner end edges and outer end edges respectively spaced apart from and opposed to each other in the longitudinal direction and extending in the transverse direction, the inner end edges of the front and rear waist panels lie closer to the crotch region than the outer end edges of the front and rear waist panels, and the inner end edges of the front and rear waist panels cooperate with lateral edges of the leg sheets extending in the longitudinal direction to define peripheries of the pair of leg-openings, wherein each of the leg sheets has an inner region adjoining to the absorbent structure and extending in the longitudinal direction, and an outer region opposite to the inner region in the transverse direction and transversely outboard of the inner region in the flatly developed state, adjoining to the inner region, and extending in the longitudinal direction, the outer regions of the leg sheets are elastic regions where a plurality of leg elastics are attached under tension to the leg sheets and extend in the longitudinal direction, the inner regions of the leg sheets are inelastic regions provided with none of the plurality of leg elastics, the leg sheets have front and rear end portions opposing each other in the longitudinal direction and joined to the front and rear waist panels, respectively, the plurality of leg elastics attached to the leg sheets join the front waist panel to the rear waist panel, in a state that the front and rear waist panels are joined to each other, the inner regions rise above the absorbent structure along the lateral edges of the absorbent structure in a thickness direction of the absorbent structure, and the outer regions are bent outwardly in the transverse direction so as to define the peripheries of the leg-openings, and the crotch panel further has first and second crotch sheets arranged below the absorbent structure, and the inelastic regions of the leg sheets are located between and directly joined to the first and second crotch sheets.

2. The wearing article according to claim 1, wherein the leg sheets are separate sheets attached to the crotch panel.

3. The wearing article according to claim 1, wherein
a dimension of each of the elastic regions in the transverse direction is 20 mm or larger, and
a dimension of each of the inelastic regions in the transverse direction is 10 mm or larger.

4. The wearing article according to claim 1, wherein the dimension of the each inelastic region in the transverse direction is in a range of 22% to 56% of a dimension of the respective leg sheet in the transverse direction.

5. The wearing article according to claim 1, wherein
an effective elongation dimension of the leg sheets at a maximum elongation point is larger than a distance dimension in the longitudinal direction from the inner end edge of the front waist region to the inner end edge of the rear waist region, and
joint regions between the leg sheets and the crotch panel are formed with a plurality of gathers extending in parallel to each other in the transverse direction.

6. The wearing article according to claim 5, wherein the effective elongation dimension of the leg sheets is in a range of about 1.05 to about 1.5 times of the distance dimension in the longitudinal direction from the inner end edge of the front waist region to the inner end edge of the rear waist region.

7. The wearing article according to claim 1, wherein
the leg sheets respectively further include cover sheets to which the leg elastics are attached,
the leg sheets are attached to the inner end edges of the front and rear waist regions in an elastically contracted state and are formed with a plurality of gathers extending in the transverse direction and folds repeating in the longitudinal direction, and
joint regions between the leg sheets and the crotch panel are formed with the plurality of gathers extending in the transverse direction.

8. The wearing article according to claim 1, wherein
the leg sheets respectively include cover sheets to which the leg elastics are attached, and
the leg sheets are attached to the inner end edges of the front and rear waist regions in a state of being mechanically formed with gathers extending in the transverse direction and folds repeating in the longitudinal direction.

9. The wearing article according to claim 1, wherein
the front waist region has
a pair of first elastic zones extending in the transverse direction along the inner end edge of the front waist region and spaced apart from each other in the transverse direction and
a first inelastic zone extending between the first elastic zones;
the rear waist region has
a pair of second elastic zones extending in the transverse direction along the inner end edge of the rear waist region and spaced apart from each other in the transverse direction and
a second inelastic zone extending between the second elastic zones;
the leg elastics intersect with the first and second elastic zones and a dimension in the transverse direction of the second inelastic zone is larger than a dimension in the transverse direction of the first inelastic zone; and
a dimension in the transverse direction of respective first intersection zones, in which the first elastic zones intersect with the leg elastics, is larger than a dimension in the transverse direction of respective second intersection zones, in which the second elastic zones intersect with the leg elastics.

10. The wearing article according to claim 9, wherein a dimension in the transverse direction of the respective second intersection zones in the rear waist region is in a range of about 10 to about 30% of a dimension in the transverse direction of the leg elastics.

11. The wearing article according to claim 9, wherein
the absorbent structure lies in a midsection of the crotch panel in the transverse direction,
the first elastic zones extend from opposite lateral edges of the front waist region to the absorbent structure, and the second elastic zones extend from opposite lateral edges of the rear waist region to the leg elastics.

12. The wearing article according to claim 9, wherein a tensile stress at a maximum elongation point of at least the second elastic zones of the first and second elastic zones is higher than a tensile stress at a maximum elongation point of elastic zones defined by the leg elastics.

13. The wearing article according to claim 1, wherein a dimension of the leg sheets in the longitudinal direction is smaller than a dimension of the absorbent structure in the longitudinal direction.

14. The wearing article according to claim 1, wherein a dimension of the front waist region in the longitudinal direction is substantially the same as a dimension of the rear waist region in the longitudinal direction, and
the inner end edges of the front and rear waist regions rectilinearly extending in the transverse direction are substantially orthogonal to the leg elastics.

15. The wearing article according to claim 1, wherein each of the leg sheets includes
a cover sheet to which the leg elastics are attached, and inner and outer lateral edge portions opposing each other in the transverse direction, and
in each of the leg sheets, the leg elastics are joined to the cover sheet at the outer lateral edge portion of the leg sheet.

16. A disposable wearing article having a longitudinal direction and a transverse direction, said disposable wearing article comprising:
a front waist region;
a rear waist region;
a crotch region extending between the front and rear waist regions;
an annular elastic waist panel including a front waist panel and a rear waist panel joined to each other so as to define the front and rear waist regions;
a crotch panel joined to the elastic waist panel so as to define the crotch region;
an absorbent structure joined to the front and rear waist panels and the crotch panel; and
a pair of leg-openings' peripheries lying on both sides of the crotch region in the transverse direction,
wherein
the crotch panel has a pair of leg sheets extending in the longitudinal direction along lateral edges of the absorbent structure,
in a state that the wearing article is flatly developed after the front and rear waist panels have been disjoined from each other,
the front and rear waist panels have inner end edges and outer end edges respectively spaced apart from and opposed to each other in the longitudinal direction and extending in the transverse direction,
the inner end edges of the front and rear waist panels lie closer to the crotch region than the outer end edges of the front and rear waist panels, and
the inner end edges of the front and rear waist panels cooperate with lateral edges of the leg sheets extending in the longitudinal direction to define the pair of leg-openings' peripheries,
wherein
each of the leg sheets has
an inner region adjoining to the absorbent structure and extending in the longitudinal direction and
an outer region opposite to the inner region in the transverse direction and transversely outboard of the inner region in the flatly developed state, adjoining to the inner region, and extending in the longitudinal direction,
in a state that the front and rear waist panels are joined to each other,
the inner regions rise above the absorbent structure along the lateral edges of the absorbent structure in a thickness direction of the absorbent structure, and
the outer regions are bent outwardly in the transverse direction so as to define the leg-openings' peripheries,
the leg sheets are elasticized leg sheets provided with a plurality of leg elastics,
the outer regions of the respective leg sheets are elastic regions in which the plurality of the leg elastics are attached under tension so as to extend in the longitudinal direction,
the inner regions are inelastic regions provided with none of the leg elastics,
the inelastic regions rise above the absorbent structure along the lateral edges of the absorbent structure in the thickness direction of the absorbent structure,
the elastic regions are bent outwardly of the article in the transverse direction so as to form the leg-openings' peripheries,
the front waist region has
a pair of first elastic zones extending in the transverse direction along the inner end edge of the front waist region and spaced apart from each other in the transverse direction and
a first inelastic zone extending between the first elastic zones;
the rear waist region has
a pair of second elastic zones extending in the transverse direction along the inner end edge of the rear waist region and spaced apart from each other in the transverse direction and
a second inelastic zone extending between the second elastic zones;
the leg elastics intersect with the first and second elastic zones and a dimension in the transverse direction of the second inelastic zone is larger than a dimension in the transverse direction of the first inelastic zone; and
a dimension in the transverse direction of respective first intersection zones, in which the first elastic zones intersect with the leg elastics, is larger than a dimension in the transverse direction of respective second intersection zones, in which the second elastic zones intersect with the leg elastics.

17. The wearing article according to claim 16, wherein a dimension in the transverse direction of the respective second intersection zones in the rear waist region is in a range of about 10 to about 30% of a dimension in the transverse direction of the leg elastics.

18. The wearing article according to claim 16, wherein the absorbent structure lies in a midsection in the transverse direction of the crotch panel,
the first elastic zones extend from opposite lateral edges of the front waist region to the absorbent structure, and
the second elastic zones extend from opposite lateral edges of the rear waist region to the leg elastics.

19. The wearing article according to claim 16, wherein a tensile stress at the maximum elongation point of at least the second elastic zones of the first and second elastic zones is higher than a tensile stress at the maximum elongation point of elastic zones defined by the leg elastics.

* * * * *